United States Patent
Kassab

(10) Patent No.: US 9,974,459 B2
(45) Date of Patent: May 22, 2018

(54) LOCALIZATION OF BODY LUMEN JUNCTIONS

(75) Inventor: Ghassan S. Kassab, Zionsville, IN (US)

(73) Assignee: 3DT Holdings, LLC, San Diego, CA (US)

( * ) Notice: Subject to any disclaimer, the term of this patent is extended or adjusted under 35 U.S.C. 154(b) by 1358 days.

(21) Appl. No.: 12/305,520

(22) PCT Filed: Jun. 29, 2007

(86) PCT No.: PCT/US2007/015239
§ 371 (c)(1),
(2), (4) Date: Dec. 18, 2008

(87) PCT Pub. No.: WO2008/005388
PCT Pub. Date: Jan. 10, 2008

(65) Prior Publication Data
US 2009/0182287 A1    Jul. 16, 2009

Related U.S. Application Data

(63) Continuation-in-part of application No. 11/063,836, filed on Feb. 23, 2005, now Pat. No. 7,818,053, and
(Continued)

(51) Int. Cl.
*A61B 5/05*    (2006.01)
*A61B 5/042*   (2006.01)
(Continued)

(52) U.S. Cl.
CPC ........ *A61B 5/0422* (2013.01); *A61B 5/02007* (2013.01); *A61B 5/053* (2013.01);
(Continued)

(58) Field of Classification Search
CPC ...... A61B 5/0537; A61B 5/053; A61B 5/4872
(Continued)

(56) References Cited

U.S. PATENT DOCUMENTS

| 4,562,843 A | * | 1/1986 | Djordjevich | ......... | A61B 5/0205 |
|---|---|---|---|---|---|
| | | | | | 600/485 |
| 4,660,571 A | | 4/1987 | Hess et al. | | |

(Continued)

FOREIGN PATENT DOCUMENTS

EP          1025805         8/2000

OTHER PUBLICATIONS

International Searching Authority, International Search Report, dated Mar. 21, 2008 (PCT/US2007/015239).
(Continued)

*Primary Examiner* — Daniel Cerioni
(74) *Attorney, Agent, or Firm* — Reichel Stohry LLP; Mark C. Reichel; Natalie J. Dean

(57) ABSTRACT

Devices, systems, and methods for the localization of body lumen junctions and other intraluminal structure are disclosed. Various embodiments permit clinicians to identify the locations of intraluminal structures and medical devices during non-surgical medical techniques, such as cardiac ablation, by determining the intralumen conductance and/or cross-sectional area at a plurality of locations within the body lumen.

81 Claims, 11 Drawing Sheets

Related U.S. Application Data a continuation-in-part of application No. 10/782,149, filed on Feb. 19, 2004, now Pat. No. 7,454,244.

(60) Provisional application No. 60/817,422, filed on Jun. 30, 2006, provisional application No. 60/449,266, filed on Feb. 21, 2003, provisional application No. 60/493,145, filed on Aug. 7, 2003, provisional application No. 60/502,139, filed on Sep. 11, 2003.

(51) Int. Cl.

| | |
|---|---|
| A61B 5/02 | (2006.01) |
| A61B 5/053 | (2006.01) |
| A61B 5/107 | (2006.01) |
| A61B 18/14 | (2006.01) |
| A61B 18/00 | (2006.01) |

(52) U.S. Cl.
CPC .......... *A61B 5/0538* (2013.01); *A61B 5/1076* (2013.01); *A61B 18/1492* (2013.01); *A61B 2018/00875* (2013.01); *A61B 2018/1467* (2013.01)

(58) Field of Classification Search
USPC .... 600/300, 301, 481, 547, 454; 606/41, 23, 606/24
See application file for complete search history.

(56) References Cited

U.S. PATENT DOCUMENTS

| | | | |
|---|---|---|---|
| 5,453,576 | A | 9/1995 | Krivitski |
| 6,270,493 | B1 | 8/2001 | Lalonde et al. |
| 6,494,832 | B1 | 12/2002 | Feldman et al. |
| 2002/0129952 | A1 | 9/2002 | Matsudate et al. |
| 2005/0171446 | A1* | 8/2005 | Krivitski ................ A61B 17/22 600/504 |
| 2006/0009759 | A1 | 1/2006 | Christian et al. |
| 2006/0271090 | A1* | 11/2006 | Shaked ............ A61B 17/12022 606/192 |
| 2009/0062684 | A1* | 3/2009 | Gregersen et al. ........... 600/547 |

OTHER PUBLICATIONS

International Searching Authority, Written Opinion of the International Searching Authority, dated Mar. 21, 2008 (PCT/US2007/015239).

International Searching Authority, International Search Report, dated Apr. 7, 2008 (PCT/US2007/015239).

International Searching Authority, Written Opinion of the International Searching Authority, dated Apr. 7, 2008 (PCT/US2007/015239).

\* cited by examiner

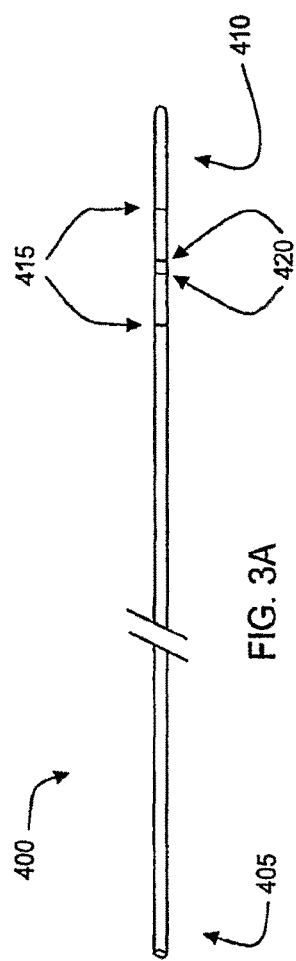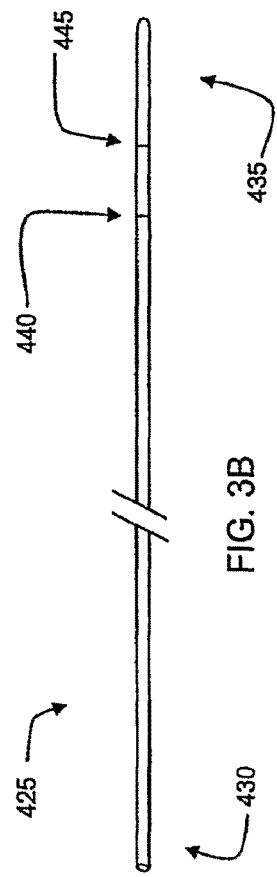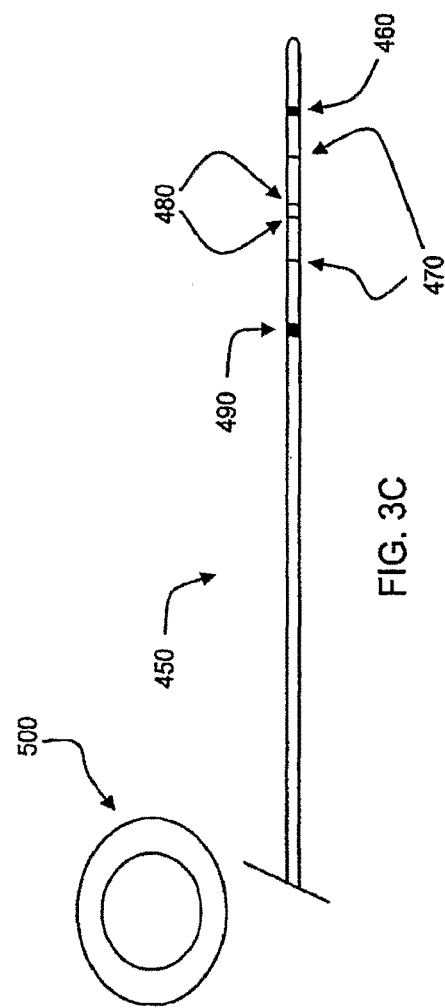

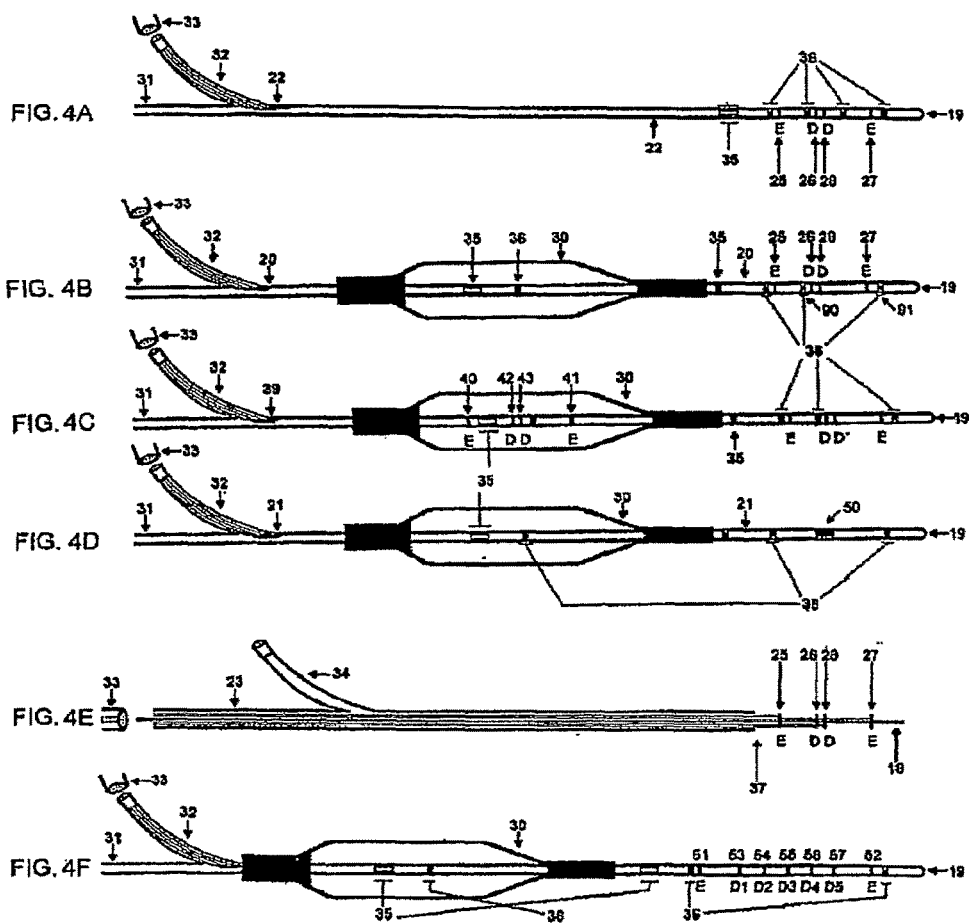

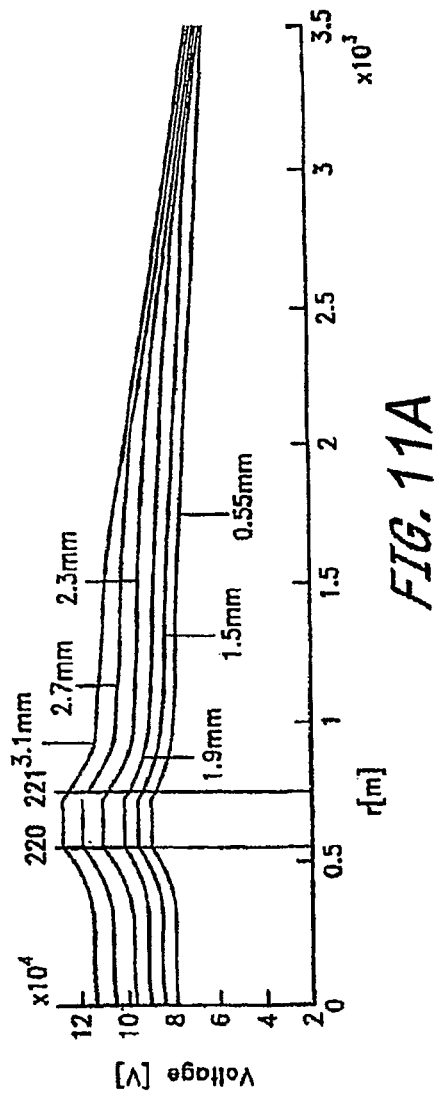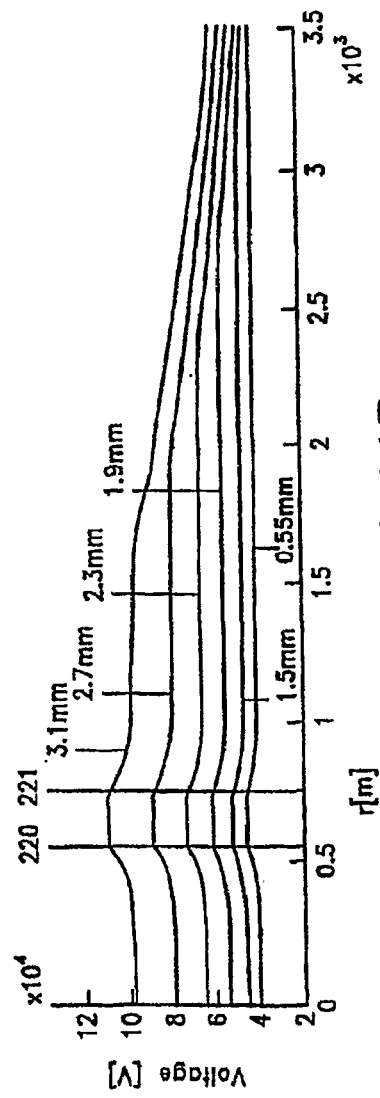

LOCALIZATION OF BODY LUMEN JUNCTIONS

The present application is a U.S. National Stage Application of International Patent Application Serial No. PCT/US2007/015239, filed Jun. 29, 2007, which claims priority to U.S. Provisional Patent Application Ser. No. 60/817,422, filed Jun. 30, 2006, and which also claims priority to and is a continuation-in-part of U.S. patent application Ser. No. 11/063,836, filed Feb. 23, 2005 and issued as U.S. Pat. No. 7,818,053 on Oct. 19, 2010, which claims priority to and is a continuation-in-part of U.S. patent application Ser. No. 10/782,149, filed Feb. 19, 2004, issued as U.S. Pat. No. 7,454,244 on Nov. 18, 2008, which claims priority to U.S. Provisional Patent Application Ser. No. 60/449,266, filed Feb. 21, 2003, U.S. Provisional Patent Application Ser. No. 60/493,145, filed Aug. 7, 2003, and U.S. Provisional Patent Application Ser. No. 60/502,139, filed Sep. 11, 2003. The contents of each of these applications are hereby incorporated by reference in their entirety into this disclosure.

BACKGROUND

Atrial fibrillation ("AF") of the human heart is a common arrhythmia which is estimated to affect anywhere from 2.2 million to about 5.1 million Americans, as well as approximately 5% of the elderly population over 69 years of age. Theoretically, the AF mechanism involves two main processes: (1) higher automaticity in one or more rapidly depolarizing foci and (2) reentry of conduction involving one or more circuits. Rapid atrial foci, often located in at least one of the superior pulmonary veins, can begin AF in predisposed patients. In addition, the "multiple-wavelet hypothesis" has been proposed as a potential mechanism for AF caused by conduction reentry. According to the hypothesis, normal conduction wave fronts break up, resulting in a number of self-perpetuating "daughter" wavelets that spread through the atria causing abnormal contraction of the myocardium.

Surgical treatment of AF requires the construction of barriers to conduction within the right atrium and left atrium to restrict the amount of myocardium available to spread reentrant wave fronts, thereby inhibiting sustained AF. By making incisions in the myocardium, conduction is interrupted. Since it has been demonstrated that the pulmonary veins often contain the specific rapidly-depolarizing loci, incisions encircling the pulmonary veins can help prevent AF. Similarly, potentially arrhythmogenic foci close to the pulmonary veins, as well as specific atrial regions with the shortest refractory periods, may be isolated from the rest of the atria by strategically placed incisions. Although the risk of such surgery alone is typically less than 1%, the need for median sternotomy and the use of cardiopulmonary bypass, as well as a risk of short-term fluid retention, make this procedure less than ideal.

As an alternative to surgery, catheter ablation has evolved as a standard therapy for patients at high risk for ventricular and supraventricular tachyarrhythmia. The recognition that foci triggering AF frequently initiate within the pulmonary veins has led to ablation strategies that target this zone or that electrically isolate the pulmonary veins from the left atrium. In the superior vena cava, the right atrium, left atrium, and coronary sinus were found as other sites of arrhythmogenic foci. The frequency of recurrent AF has been reduced in more than 60% of patients by the ablation of the foci (superior vena cava, the right and left atria, and the coronary sinus). However, the risk of recurrent AF following a focal ablation procedure is still between 30% to 50% over the first year and is even higher when the ablation involves an attempt to isolate more than one pulmonary vein.

In most circumstances, the cardiac ablation catheter is inserted into a blood vessel (artery or vein), usually through an entry site located in the upper leg or neck. Under fluoroscopy, the tube is navigated through the blood vessels until it reaches the heart. In the heart, electrodes at the catheter tip gather data that pinpoint the location of faulty tissue in the heart (electrical mapping). Once the site is identified, the device delivers either radiofrequency energy (RF ablation) or intense cold (cryoablation) to destroy the small section of tissue. The major goal of this procedure is segmental pulmonary vein isolation and circumferential pulmonary vein ablation. The circumferential ablation strategy yields either an atriovenous electrical disconnection, as demonstrated by elimination of pulmonary vein ostial potentials and absence of discrete electrical activity inside the lesion during pacing from outside the ablation line, or a profound atrial electroanatomical remodeling as expressed by voltage abatement inside and around the encircled areas involving to some extent the posterior wall of the left atrium. The endpoint is the electrical isolation of the pulmonary veins from the left atrium, as they house foci triggering AF in about 80% to about 95% of cases and seem to play a key role in arrhythmia maintenance.

Possible complications of catheter ablation for AF include systemic embolism, pulmonary vein stenosis, pericardial effusion, cardiac tamponade, and phrenic nerve paralysis. The majority of these risks stem from the ablation of an incorrect region. Hence, proper navigation during cardiac ablation is one of the greatest challenges for the electrophysiologist performing the procedure.

Visualization of endocardial structure and ablation lesions through flowing blood has been an obstacle for proper navigation during cardiac ablation. Currently, clinicians perform cardiac ablation using intracardiac echo based on ultrasound. A catheter is advanced from the femoral vein into the heart, thereby allowing the clinician to observe the heart from the inside. This method enables good anatomy imaging, and the clinician can view the electrode-tissue interface during the ablation. Despite this technology, however, the clinician cannot have complete certainty after the ablation procedure that the procedure created a permanent lesion that has destroyed only the targeted tissue and nothing more.

Another method used to determine the accuracy of the ablation is to compare the electrical signals in the heart before and after the procedure to determine whether certain arrhythmogenic signals have been eliminated. However, this method does not always provide sufficient evidence that a permanent lesion has been created as a result of the ablation.

Thus, these approaches fall short of providing optimum clarity and accuracy regarding the ablation. Furthermore, conventional technologies do not combine the function of direct visualization and ablation into one catheter, but instead require the use and coordination of multiple catheters, thereby inherently increasing the risks to the patient.

A new technique has emerged that allows an electrophysiologist to create a real-time 3-D electroanatomical cardiac map using GPS-like technology called CARTO™. The created map is then merged with CT or MRI images providing detailed structures of the chambers of the heart. Real-time intracardiac echocardiography, along with fluoroscopy, is also used to enhance the safety and efficacy of the procedure. Another system, called the Localisa® Intracardiac Navigation System, allows a user to continuously monitor mapping and ablation catheter positions, thus facilitating pulmonary vein isolation procedures and reducing radiation exposure to the patient and medical personnel.

Although these newer systems have significant potential, they are generally unavailable to the typical electrophysiology laboratory because of cost. Thus, there is a need for an efficient, easy to use, and reasonably priced technique for localization and ablation that can be adapted for use in virtually any clinic.

BRIEF SUMMARY

Various embodiments of devices, systems, and methods for localization of body lumen junctures are disclosed herein. At least some of the disclosed embodiments allow a clinician to identify a body lumen junction, such as a pulmonary vein-atrial junction, or other desired anatomical structures, to a higher spatial resolution than with conventional techniques. Thus, subsequent ablation may be performed using the same device that presented a visual signal of the junction, thereby decreasing the tools required for proper location and ablation of the junction and targeted tissue.

Some embodiments disclosed herein include systems for localizing a body lumen junction or other intraluminal structure. These systems comprise a catheter having a proximal end and a distal end for placement into a body lumen. The catheter may comprise a first electrode and a second electrode, and each of the first and second electrodes have a proximal end and a distal end; the distal ends of the first and second electrodes are located between the proximal and distal ends of the catheter. The system further comprises a processor connected to the first and second electrodes of the catheter. The processor is capable of collecting conductance data to determine a profile of the body lumen. The conductance data is collected at a plurality of locations within the body lumen and determined at each of the plurality of locations when the distal ends of the first and second electrodes are immersed in a fluid within the body lumen. In some embodiments, the processor is also capable of calculating a cross-sectional area of the body lumen at each of the plurality of locations within the body lumen using the conductance data.

For certain embodiments of such systems, the relevant body lumen comprises at least a portion of an atrium, a pulmonary vein-atrial junction, a blood vessel, a biliary tract, or an esophagus. Indeed, many embodiments may be used in connection with any other body lumen that is suitable for access and localization.

The body lumen may have at least some fluid inside, and the fluid may comprise blood or another suitable fluid, such as a solution of NaCl having a known conductivity. Certain embodiments of the catheter have a passageway for passing fluid through the catheter to the location of the distal ends of the first and second electrodes, such that the fluid passing through the passageway comes in contact with the distal ends of the first and second electrodes. For some embodiments, the conductance data is determined at each of a plurality of locations within the lumen when the distal ends of the first and second electrodes are immersed in a first fluid having a first conductivity and then a second fluid having a second conductivity. The conductance data may comprise a first conductance value determined at each of the plurality of locations when the distal ends of the first and second electrodes are immersed in the first fluid and a second conductance value determined at each of the plurality of locations when the distal ends of the first and second electrodes are immersed in the second fluid. The profile of the body lumen is therefore determined from the first and second conductance values collected from each of the plurality of locations, the first conductivity of the first fluid, and the second conductivity of the second fluid. The profile may consist of actual or relative values for cross-sectional areas or conductances.

Many embodiments disclosed herein have a catheter with at least four electrodes, including at least two excitation electrodes and at least two detection electrodes. Each of the electrodes has a proximal end and a distal end, wherein the proximal ends of the electrodes may be connected to the processor directly or indirectly. In at least some embodiments, the distal ends of the excitation electrodes are located between the proximal and distal ends of the catheter, and the distal ends of the detection electrodes are located between the distal ends of the excitation electrodes.

Certain of the disclosed embodiments have at least one ablation contact positioned at the distal end of the catheter, enabling the clinician to perform an ablation immediately following localization without having to change catheters. The one or more ablation contacts are configured to remove or destroy a targeted tissue within the body lumen, such as by heating the tissue, freezing the tissue using cryoablation, mechanically destroying or removing the tissue, or by delivering an electrical charge to the tissue. With respect to embodiments using electricity for ablation, an adhesive grounding pad may be attached to the outside of the patient's body in order to conduct the electrical charge from the targeted tissue.

The targeted tissue may include tissue that is located at, or adjacent to, a pulmonary vein-atrial junction. Such tissue may at least partially surround the junction, and may substantially surround the junction. For proper location of the ablation, the ablation contact may be positioned circumferentially around a substantially circular portion of the catheter. In some embodiments the catheter includes more than one ablation contact.

Certain embodiments disclosed herein include a number of steps for localizing a junction or other structure within a body lumen, including providing an embodiment of a system as disclosed herein; introducing the catheter into the body lumen; providing electrical current flow to the body lumen through the catheter; measuring a first conductance value at a first location in the body lumen; moving the catheter to a second location in the body lumen; measuring a second conductance value at a second location in the body lumen; and determining a profile of the body lumen based on the first conductance value of the first location and the second conductance value of the second location. The profile of the body lumen resulting from such embodiments may include relative conductances and/or relative cross-sectional areas.

For other embodiments, the actual values for the lumen conductance or cross-sectional area are determined by further injecting a known volume of a first solution having a first conductivity into the body lumen; injecting a second solution having a second conductivity into the body lumen, wherein the second solution has a second volume and wherein the second conductivity does not equal the first conductivity; measuring a second conductance value at the first location in the body lumen; calculating the conductance at the first location in the body lumen; measuring a first conductance value at a second location in the body lumen; and calculating the conductance at the second location in the body lumen. The determination of the profile of the body lumen may be based on the conductance of the first location, the conductance of the second location, and the conductivities of the first and second solutions. In addition, in some embodiments, the tissue is ablated after localization using the same catheter for both aspects of the procedure.

BRIEF DESCRIPTION OF THE DRAWINGS

FIG. 3A shows an embodiment of a catheter for localization of a body lumen juncture;

FIG. 3B shows another embodiment of a catheter for localization of a body lumen juncture;

FIG. 3C shows an embodiment of a catheter for localization and ablation of a body lumen juncture;

FIG. 4A shows another embodiment of a catheter for localization;

FIG. 4B shows an embodiment of a balloon catheter having impedance measuring electrodes supported in front of the stenting balloon;

FIG. 4C shows another embodiment of a balloon catheter having impedance measuring electrodes within and in front of the balloon;

FIG. 4D shows an embodiment of a catheter having an ultrasound transducer within and in front of the balloon;

FIG. 4E shows an embodiment of a guide catheter with wire and impedance electrodes;

FIG. 4F shows an embodiment of a catheter with multiple detection electrodes;

FIG. 11A shows the voltage recorded by a conductance catheter with a radius of 0.55 mm for various size vessels (vessel radii of 3.1, 2.7, 2.3, 1.9, 1.5 and 0.55 mm for the six curves, respectively) when a 0.5% NaCl bolus is injected into the treatment site; and FIG. 11B shows the voltage recorded by a conductance catheter with a radius of 0.55 nm for various size vessels (vessel radii of 3.1, 2.7, 2.3, 1.9, 1.5 and 0.55 mm for the six curves, respectively) when a 1.5% NaCl bolus is injected into the treatment site.

DETAILED DESCRIPTION

Figure 1:
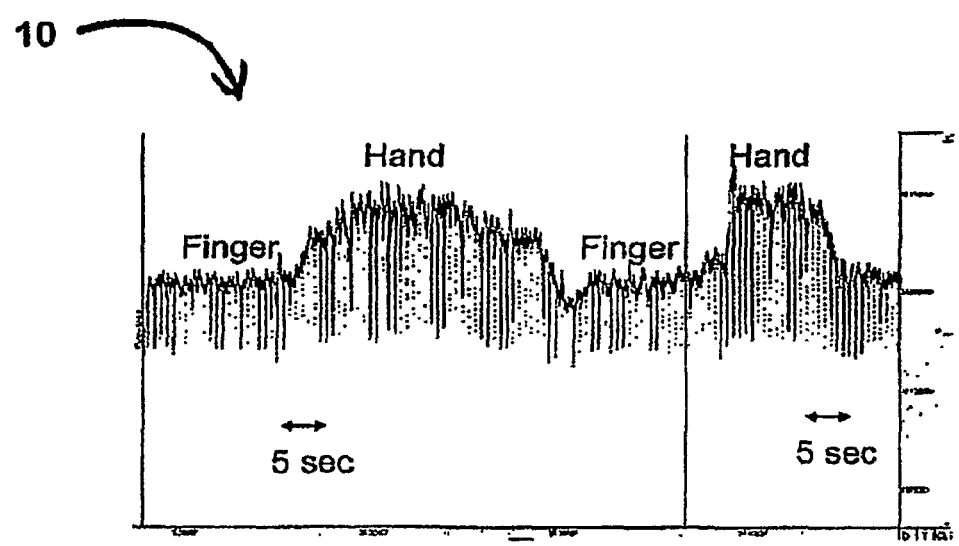
FIG. 1 shows the visual output of an embodiment of a catheter system for localization during an experiment of movement through an interior of a surgical glove.

It will be appreciated by those of skill in the art that the following detailed description of the disclosed embodiments is merely exemplary in nature and is not intended to limit the scope of the appended claims.

During various medical procedures involving intraluminal insertion of catheters or other devices, proper navigation of the device through body lumens, such as blood vessels or the heart, is critical to the success of the procedure. Indeed, unless the tissue targeted for treatment or diagnosis during the procedure is properly located, the procedure can be ineffective or, even worse, damaging to nearby healthy tissue. Therefore, a number of the embodiments disclosed herein permit a clinician to readily locate a catheter, such as an ablation catheter, or other medical device within a body lumen in relation to body lumen junctions or other anatomical structures within the lumen. This leads to proper localization of targeted tissue and increased favorable outcomes.

Some of the disclosed embodiments measure electrical conductance within the body lumen and display a profile of relative conductance values, while other embodiments use conductance data to calculate luminal cross-sectional areas and display a profile of relative cross-sectional areas along a portion of the lumen. These profiles enable the clinician to readily locate the targeted tissue for further treatment, such as ablation. In some embodiments, the conductance catheter and the ablation catheter is combined into one device so that ablation can occur immediately following localization, without requiring a change of catheters.

Many of the disclosed embodiments do not calculate an absolute value for a lumen's cross-sectional area, but instead measure electrical conductance through a portion of the lumen to form a profile of the lumen. Often, the profile comprises relative conductances taken along the lumen. However, because conductance is proportional to cross-sectional area, as explained herein, the profile can comprise relative cross-sectional areas that have been determined from the conductances taken along the lumen.

By monitoring the profile during catheterization, the clinician can visualize the anatomical structure of the lumen. For example, using a push through or a pull back of a disclosed embodiment of a catheter through a lumen, a clinician is able to localize a junction or other architectural marker in the body lumen. Such a push through or pull back will reflect, in relative terms, the lumen's changes in conductance, and therefore its changes in cross-sectional area, as the catheter moves, thereby depicting changes in lumen structure across a distance. Based on such changes in lumen structure, a clinician can determine the locations of various anatomical markers of the lumen, as well as the location of the catheter in relation to those markers. For example, localization of the junction between the relatively small pulmonary veins and the significantly larger atrium is possible by assessing the change in conductance (and therefore in cross-sectional area) of the lumen as the catheter is pushed through the vein into the atrium.

Once a specific lumen junction or other anatomical structure is localized, the clinician can better treat a targeted tissue at or near that identifying structure. Such treatment may include, for example, ablation, localized drug delivery, angioplasty, or stent delivery. One common use of ablation is to electrically isolate arrhythmogenic foci, which are often found in the superior pulmonary veins, from the left atrium to prevent atrial fibrillation in at-risk patients. To isolate the vein and prevent further arrhythmogenic conduction from the foci, the cardiac tissue surrounding the pulmonary vein at or adjacent to the pulmonary vein-atrial junction is ablated. Ablation can be performed in a number of ways, including mechanically, electrically, using heat, or using cryoablation. Regardless of the method for removing or destroying the targeted tissue, the clinician preparing to ablate an area of cardiac tissue surrounding a pulmonary vein must direct the ablation device, often a catheter configured for ablation, to the targeted tissue surrounding the pulmonary vein-atrial junction.

Various devices, systems, and methods for localization of body lumen junctures disclosed herein permit the clinician to accurately locate the pulmonary vein-atrial junction, as well as confirm the location of the ablation catheter with respect to the junction (and, therefore, the targeted tissue). Indeed, localization using the disclosed embodiments will minimize undesired ablation into the pulmonary veins, which causes shrinkage of collagen and hence pulmonary vein stenosis. It will also minimize the ablation of the atrium too far from the pulmonary vein, where the ablation circumference is too large and isolation of conductance is unlikely.

Experiments have demonstrated the ability of the disclosed embodiments to provide accurate and reliable feedback as to the location of a catheter within a body lumen. For instance, a surgical glove was filled with saline to simulate a left atrium (the palm) and pulmonary veins (the fingers). A catheter configured for localization as described herein was pulled back from inside a finger to the palm, thereby simulating the transition from a pulmonary vein to the atrium. FIG. 1 shows the conductance profile 10 as the catheter was pulled back from a finger into the palm of the glove, then was pushed into a finger. As can be seen, the profile shows that the conductance of the palm was significantly larger than the conductance of the finger, and the transition or demarcation from the finger to the palm is apparent. Because conductance and cross-sectional area are proportional (as discussed below), conductance profile 10 is proportional to the CSA profile (not shown) and distinguishes between the smaller cross-sectional area of the fingers and the larger cross-sectional area of the palm.

Figure 2:
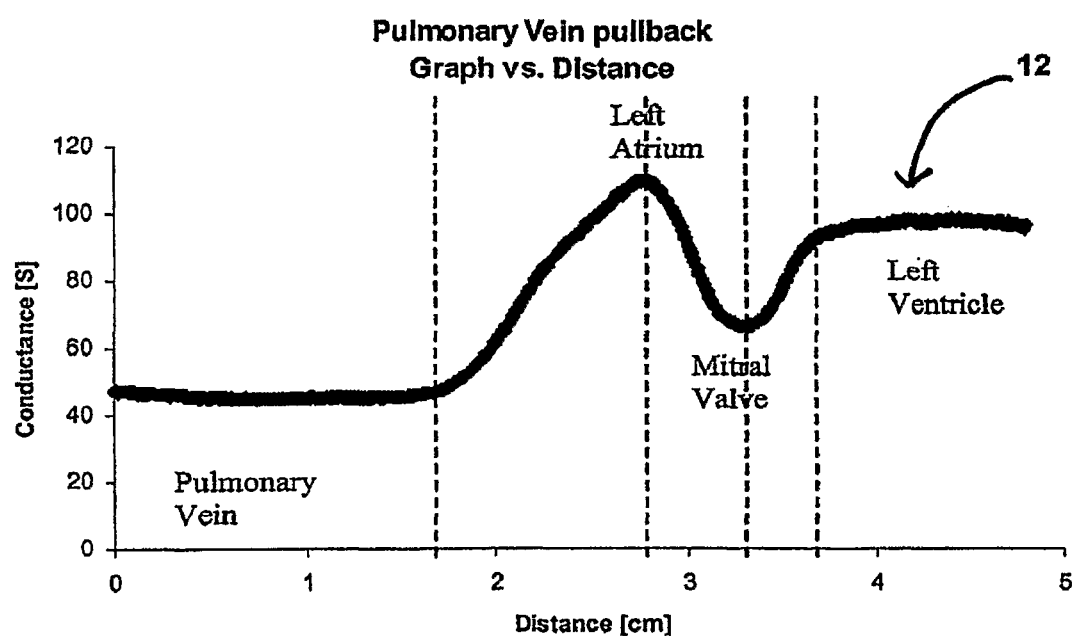
FIG. 2 shows the visual output of an embodiment of a catheter system for localization during an experiment of movement through an interior of a heart.

A similar pullback experiment was carried out in a heart. Starting from the pulmonary vein, a catheter configured for localization as described herein was pulled back from the pulmonary vein into the left atrium and ventricle. FIG. 2 shows a conductance tracing 12 that reflects the conductance for each region of the body lumen as the catheter is pulled back over a distance of about 5 cm from a starting point in the pulmonary vein. The pulmonary vein can be clearly identified by reference to its relative conductance compared to those of the left atrium, the mitral valve, and the left ventricle. Indeed, the atrial CSA is significantly larger than that of the pulmonary vein, and the atrial CSA increases with distance away from the pulmonary vein-atrial junction. A reduction in CSA is then observed as the catheter approaches and crosses the mitral valve. Once the catheter progresses through the mitral valve into the ventricle, the CSA increases gradually.

Using conductance data like that shown in FIG. 2, a clinician is able to locate the pulmonary vein-atrial junction, and then the tissue targeted for ablation, using a localization and ablation catheter as disclosed herein. For instance, once the end of the pulmonary vein is identified using the type of conductance data shown in FIG. 2 (i.e., where the conductance begins to increase), a 2 mm to 3 mm pullback will provide an appropriate region for ablation in most situations. The axial position of the catheter can be determined by the velocity of the pullback. The exact amount of necessary pullback should be determined by the clinician on a case by case basis based on the size of the patient and other relevant factors.

A conductance or impedance catheter measures conductance within a body lumen using a number of electrodes. Referring now to FIG. 3A, there is shown a conductance catheter 400 configured to localize a body lumen junction using conductance measurements. Catheter 400 has a proximal end 405 and a distal end 410, which is suitable for introduction into a body lumen. In addition, catheter 400 includes a pair of excitation electrodes 415 and a pair of detection electrodes 420. Each of excitation electrodes 415 and detection electrodes 420 has a proximal end that is capable of attachment to a processing system (not shown) and a distal end that is located on catheter 400 between proximal end 405 and distal end 410. The distal ends of detection electrodes 420 are located on catheter 400 between the distal ends of excitation electrodes 415. Excitation electrodes 415 are configured to emit a measured electrical charge into the body lumen, while detection electrodes 420 detect the amount of the charge that travels through a fluid within the body lumen. As explained in more detail below, a processing system calculates the change in electrical charge to determine the conductance through the lumen at any given location in the lumen.

As shown in FIG. 3A, electrodes 415 and 420 are located at distal end 410 of catheter 400. However, the positioning of the electrodes is not limited to this distal end portion, but may be anywhere on the catheter that can assist in providing conductance information to the clinician. Furthermore, multiple sets of electrodes (see FIG. 4F) may also be used to provide additional information used for mapping the interior anatomical structure of an internal organ, vessel, or other body lumen.

Many embodiments disclosed herein, such as the embodiment shown in FIG. 3A, have at least two detection electrodes and two excitation electrodes. However, in the embodiment shown in FIG. 3B, only two electrodes are used. Catheter 425 has a proximal end 430 and a distal end 435, as well as a first electrode 440 and a second electrode 445. Each of electrodes 440 and 445 has a proximal end (not shown) and a distal end located on catheter 425 between proximal end 430 and distal end 435. Because catheter 425 has only two electrodes, each electrode must serve both the excitation function and the detection function. To enable a single electrode to send and measure the electric charge, a delay must be added to the circuit. Additionally, a bipolar catheter must be stationary at the time of measurement, requiring the clinician to obtain a profile by moving the catheter to a desired location, stopping and taking a measurement, and then moving the catheter again. By contrast, tetrapolar catheters may take a continuous conductance measurement as the catheter is pulled or pushed through the body lumen, thereby giving a more detailed profile as compared to bipolar catheters.

Although the embodiments shown in FIG. 3A and FIG. 3B are used primarily for localization, certain of the disclosed embodiments combine the function of localization and ablation into one catheter and thereby improve the accuracy and safety of the ablation procedure by allowing the physician to properly identify the targeted tissue for ablation before the ablation begins. For example, catheter 450 shown in FIG. 3C is a conductance catheter that is configured to both localize a body lumen junction and ablate targeted tissue at or adjacent to the junction. Catheter 450 has an ablation contact 460 for removing or destroying a targeted tissue, two excitation electrodes 470, and two detection electrodes 480, as well as a passageway 490 for passing fluid through catheter 450 to the body lumen. Each of excitation electrodes 470 and detection electrodes 480 has a proximal end (not shown) for connection to a processor and a distal end positioned on catheter 450. The distal ends of detection electrodes 480 are positioned on catheter 450 between the distal ends of excitation electrodes 470.

Although at least some embodiments can properly measure lumen conductance in the presence of a bodily fluid (such as blood) within the lumen, certain other embodiments may use fluids injected into the body lumen to properly calculate lumen conductance and/or cross-sectional area, as explained herein. Therefore, some embodiments include a channel through which fluid is injected into the body lumen. In the embodiment shown in FIG. 3C, infusion passageway 490 is configured to permit such injection so that fluid flowing from passageway 490 will flow at least to the location of the distal ends of excitation electrodes 470 and detection electrodes 480. Thus, the fluid passing through passageway 490 into the lumen will come in contact with the distal ends of excitation electrodes 470 and detection electrodes 480.

Referring again to FIG. 3C, ablation contact 460 delivers an electric current to a tissue targeted for ablation. The current passes through ablation contact 460, which is in contact with the targeted tissue, entering the targeted tissue and returning to a grounding pad electrode 500 that is positioned on the outside of the body. Grounding pad electrode 500 may be held in place using any acceptable means, including an adhesive safe for contact with human skin. Although ablation contact 460 uses electrical current to destroy targeted tissue, other types of suitable ablation methods may be used. For instance, other embodiments disclosed herein could ablate tissue using very high heat, mechanical means, or cryoablation.

Referring now to FIGS. 4A to 4F, several embodiments of catheters are illustrated. With reference to the embodiment shown in FIG. 4A, there is shown an impedance catheter 22 with four electrodes 25, 26, 27, and 28 placed close to distal end 19 of the catheter. Electrodes 25 and 27 are excitation electrodes, while electrodes 26 and 28 are detection electrodes, thereby permitting measurement of conductance (and therefore calculation of cross-sectional area) during advancement of the catheter, as described in further detail below.

In addition, catheter 22 possesses an optional infusion passageway 35 located proximal to excitation electrode 25, as well as optional ports 36 for suction of contents of the body lumen or for infusion of fluid. The fluid to inject through passageway 35 or ports 36 can be any biologically compatible fluid, but, for some circumstances disclosed herein, the conductivity of the fluid is selected to be different from that of blood.

In various embodiments, including for example the embodiment shown in FIG. 4A, the catheter contains a channel 31 for insertion of a guide wire to stiffen the flexible catheter during insertion or data recording. Additionally, channel 31 may be used to inject fluid solutions of various concentrations (and various conductivities) into the body lumen of interest. An additional channel 32 may be connected to the catheter such that the electrical wires connected to the one or more electrodes on the catheter are directed through channel 32 and to a data processor, such as data processor system 100 (see FIG. 6), through an adaptor interface 33, such as an impedance module plug or the like, as described in more detail below.

In addition to localization and ablation, some embodiments disclosed herein provide other functionality. FIGS. 4B-4F show a number of embodiments of conductance catheters having various functions. For example, several such embodiments include an angioplasty balloon, in addition to impedance electrodes (see, e.g., FIG. 4B). Such catheters may include electrodes for accurate detection of organ luminal cross-sectional area and ports for pressure gradient measurements. Hence, when using such catheters, it is not necessary to change catheters during the procedure, as with the current use of intravascular ultrasound. In at least one embodiment, the catheter can provide direct measurement of the non-stenosed area of the lumen, thereby allowing the selection of an appropriately sized stent for implantation.

With reference to the embodiment shown in FIG. 4B, four wires were threaded through one of the two lumens of catheter 20 (a 4 Fr. catheter). Catheter 20 has a proximal end and a distal end 19, as well as excitation electrodes 25, 27 and detection electrodes 26, 28 placed at or near distal end 19. Proximal to these electrodes is an angioplasty or stenting balloon 30 capable of being used to treat stenosis. The distance between the balloon and the electrodes is usually small, in the 0.5 mm to 2 cm range, but can be closer or farther away, depending on the particular application or treatment involved. The portion of catheter 20 within balloon 30 includes an infusion passageway 35 and a pressure port 36.

Detection electrodes 26 and 28 are spaced 1 mm apart, while excitation electrodes 25 and 27 are spaced 4 mm to 5 mm from either side of the detection electrodes. The excitation and detection electrodes typically surround the catheter as ring electrodes, but they may also be point electrodes or have other suitable configurations. These electrodes may be made of any conductive material, such as platinum iridium or a material with a carbon-coated surface to avoid fibrin deposits. In at least one embodiment, the detection electrodes are spaced with 0.5 mm to 1 mm between them and with a distance of between 4 mm and 7 mm to the excitation electrodes on small catheters. On large catheters, for use in larger vessels and other larger body lumens, the electrode distances may be larger. The dimensions of the catheter selected for a treatment depend on the size of the vessel or other body lumen and are preferably determined in part on the results of finite element analysis.

In one approach, dimensions of a catheter to be used for any given application depend on the optimization of the potential field using finite element analysis described below. For small organs or in pediatric patients, the diameter of the catheter may be as small as 0.3 mm. In large organs, the diameter may be significantly larger depending on the results of the optimization based on finite element analysis. The balloon will typically be sized according to the preferred dimension of the organ after the distension. The balloon may be made of materials suitable for the function, such as, for example, polyethylene, latex, polyestherurethane, or combinations thereof. The thickness of the balloon will typically be on the order of a few microns. The catheter will typically be made of PVC or polyethylene, though other materials may be used equally well. The tip of the catheter can be straight, curved, or angled to facilitate insertion into the coronary arteries or other body lumens, such as, for example, the biliary tract.

Referring again to FIG. 4B, catheter 20 may also include several miniature pressure transducers (not shown) carried by the catheter or pressure ports for determining the pressure gradient proximal to the site where the conductance is measured. The pressure is preferably measured inside the balloon and proximal to, distal to, and at the location of the conductance measurement, and locations proximal and distal thereto, thereby enabling the measurement of pressure recordings at the site of stenosis and also the measurement of pressure-difference along or near the stenosis. In one embodiment, shown in FIG. 4B, catheter 20 includes pressure port 90 and pressure port 91 proximal to or at the site of the conductance measurement for evaluation of pressure gradients. As described below with reference to FIGS. 5A, 5B, and 6, in at least one embodiment, the pressure ports are connected by respective conduits in catheter 20 to pressure sensors in the data processor system 100 (see FIG. 6). Such pressure sensors are well known in the art and include, for example, fiber-optic systems, miniature strain gauges, and perfused low-compliance manometry.

In at least one embodiment, a fluid-filled silastic pressure-monitoring catheter is connected to a pressure transducer. Luminal pressure can be monitored by a low compliance external pressure transducer coupled to the infusion channel of the catheter. Pressure transducer calibration was carried out by applying 0 and 100 mmHg of pressure by means of a hydrostatic column.

In another embodiment, shown in FIG. 4C, a catheter 39 includes another set of excitation electrodes 40, 41 and detection electrodes 42, 43 located inside the angioplastic or stenting balloon 30 for accurate determination of the balloon cross-sectional area during angioplasty or stent deployment. These electrodes are in addition to electrodes 25, 26, 27, and 28.

In various embodiments, the conductance may be measured using a two-electrode system (see FIG. 4D). In other embodiments, such as illustrated in FIG. 4F, the conductances at several locations can be measured at the same time using an array of five or more electrodes. Here, excitation electrodes 51, 52 are used to generate the current while detection electrodes 53, 54, 55, 56, and 57 are used to detect the current at their respective sites.

In another embodiment, shown in FIG. 4D, catheter 21 has one or more imaging or recording devices, such as, for example, ultrasound transducers 50 for cross-sectional area and wall thickness measurements. As shown, transducers 50 are located near distal end 19 of catheter 21.

With reference to the embodiment shown in FIG. 4E, electrodes 25, 26, 27, and 28 are built onto a wire 18, such as, for example, a pressure wire, and inserted through a guide catheter 23, where the infusion of a bolus can be made through the lumen of the guide catheter. Adaptor interface 33 may be used to house and guide the electrical wires (including proximal portions of the excitation and detection electrodes) to a data processor system 100, while a side channel 34 is used to inject various fluids into catheter 23. In yet another embodiment (not illustrated), the catheter includes a sensor for measurement of the flow of fluid in the body lumen.

Figure 9:
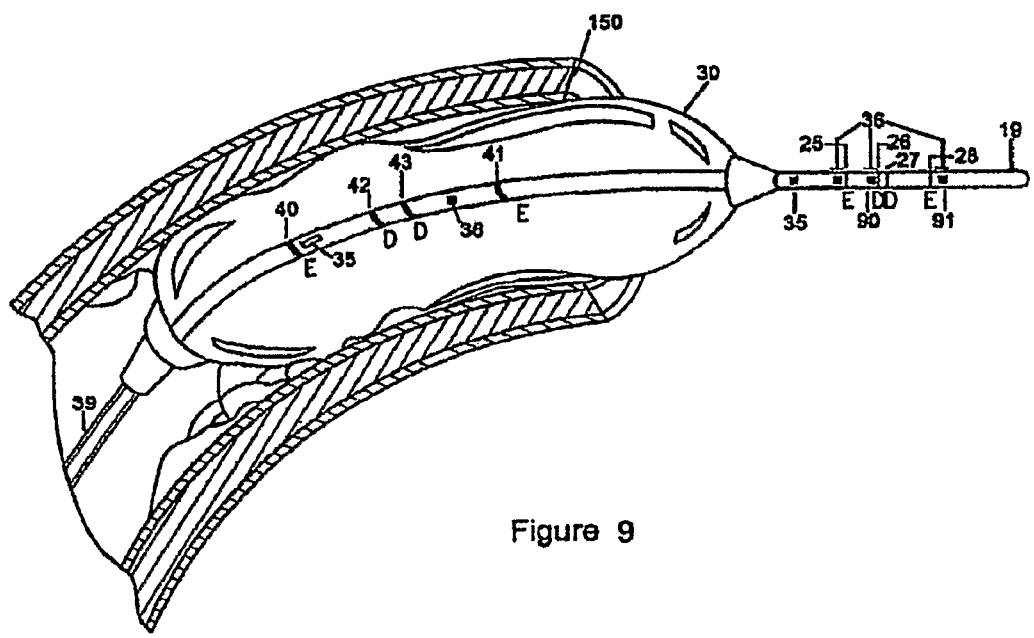
FIG. 9 shows balloon distension of the lumen of the coronary artery.
Figure 10:
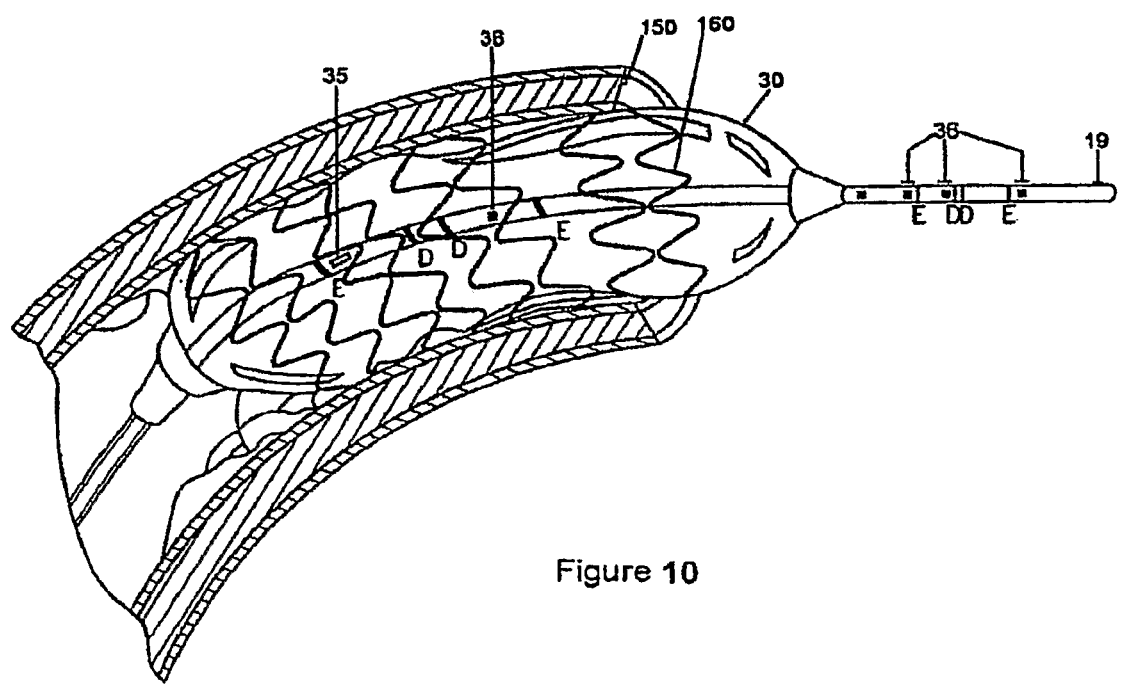
FIG. 10 shows balloon distension of a stent into the lumen of the coronary artery.

Referring now to the embodiment shown in FIG. 9, an angioplasty balloon 30 is shown distended within a coronary artery 150 for the treatment of stenosis. As described above with reference to FIG. 4C, a set of excitation electrodes 40, 41 and detection electrodes 42, 43 are located within angioplasty balloon 30. In another embodiment, shown in FIG. 10, angioplasty balloon 30 is used to distend a stent 160 within blood vessel 150.

Many of the embodiments described herein may be used as part of a system, which includes suitable connections between the system's various parts. As described below with reference to FIGS. 5A, 5B, and 6, the excitation and detection electrodes are electrically connected to electrically conductive leads in the catheter for connecting the electrodes to the data processor system 100.

Figure 5B:
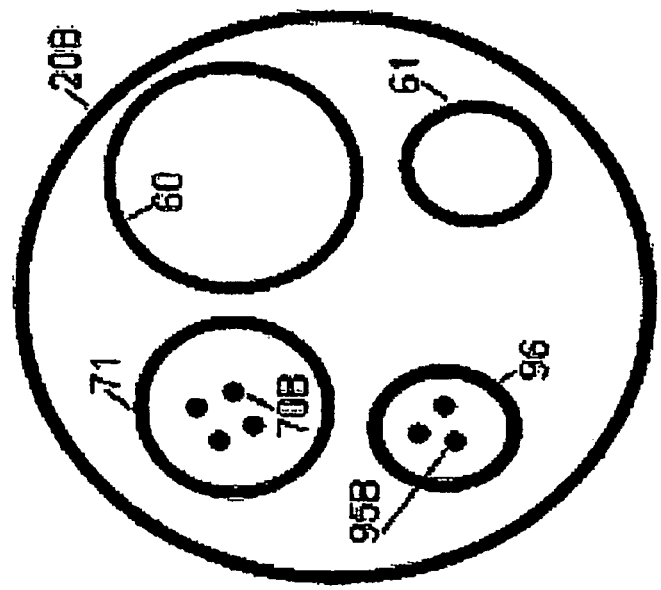
FIG. 5B shows another embodiment of a catheter in cross-section proximal to the location of the sensors showing the leads run in separate lumens.
Figure 5A:
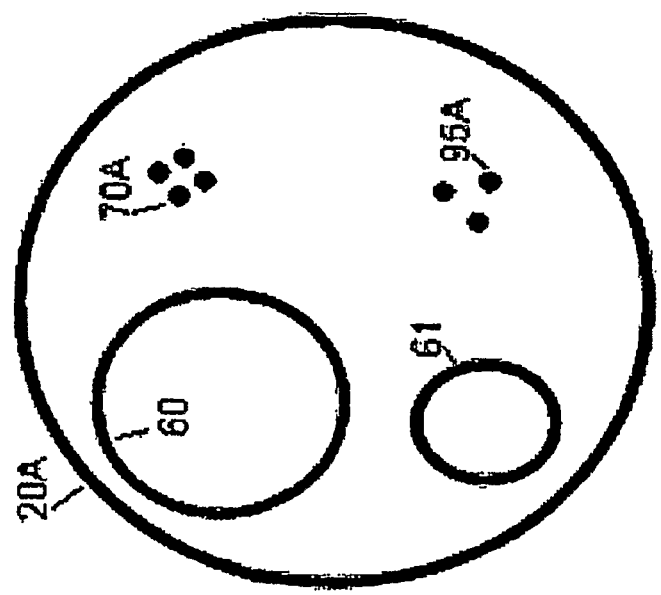
FIG. 5A shows an embodiment of a catheter in cross-section proximal to the location of the sensors showing the leads embedded in the material of the probe.

FIGS. 5A and 5B illustrate in cross-section two embodiments 20A and 20B of a catheter such as catheter 20 shown in FIG. 4B. Each embodiment has a lumen 60 for inflating and deflating the balloon and a lumen 61 for suction and infusion. The sizes of these lumens can vary. The electrode leads 70A are embedded in the material of the catheter in the embodiment shown in FIG. 5A, whereas the electrode leads 70B are tunneled through a lumen 71 formed within the body of catheter 20B shown in FIG. 5B.

Pressure conduits for perfusion manometry connect pressure ports 90, 91 to transducers included in the data processor system 100. As shown in FIG. 5A, pressure conduits 95A may be formed in catheter 20A. In another embodiment, shown in FIG. 5B, pressure conduits 95B constitute individual conduits within a tunnel 96 formed in catheter 20B. In the embodiments described above where miniature pressure transducers are carried by the catheter, electrical conductors may be substituted for these pressure conduits.

Figure 6:
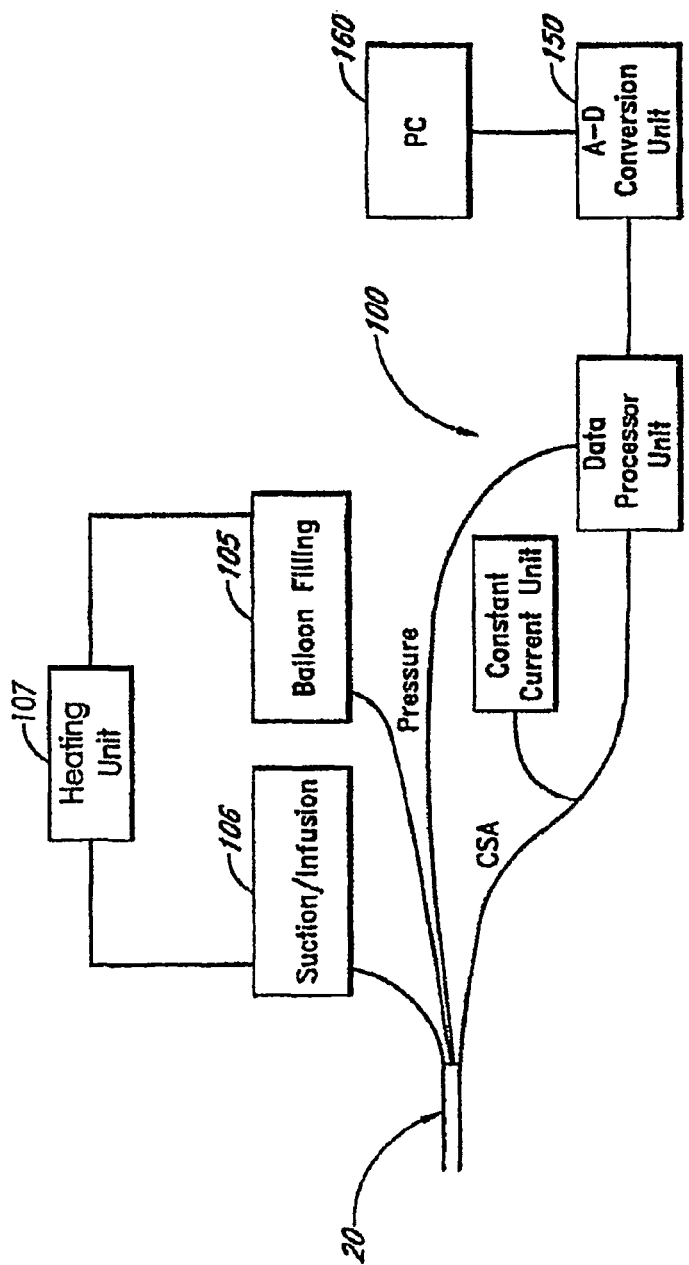
FIG. 6 is a schematic of an embodiment of a system showing a catheter carrying impedance measuring electrodes connected to a data processor equipment and excitation unit for the measurement of conductance and/or cross-sectional area.

With reference to FIG. 6, in at least some embodiments, catheter 20 connects to a data processor system 100, to a manual or automatic system 105 for distension of the balloon, and to a system 106 for infusion of fluid or suction of blood or other bodily fluid. The fluid for infusion may be heated with heating unit 107 to between 37° C. and 39° C. or to body temperature. The impedance planimetry system typically includes a constant current unit, amplifiers, and signal conditioners, but variations are possible. The pressure system typically includes amplifiers and signal conditioners. The system can optionally contain signal conditioning equipment for recording of fluid flow in the body lumen.

In at least one embodiment, the system is pre-calibrated and a catheter is available in a package. The package also may contain sterile syringes with fluids to be injected. The syringes are attached to the machine, and after heating of the fluid by the machine and placement of the catheter in the body lumen of interest, the user presses a button that initiates the injection with subsequent computation of the desired parameters. The CSA, parallel conductance, and/or other relevant measures, such as distensibility, tension, etc., will typically appear on the display panel in the PC module 160. The user can then remove the stenosis by distension or by placement of a stent.

If more than one CSA is measured at the same time, the system can contain a multiplexer unit or a switch between CSA channels. In at least one embodiment, each CSA measurement or pressure measurement will be through separate amplifier units.

In at least one embodiment, the impedance and pressure data are analog signals which are converted by analog-to-digital converters 150 and transmitted to a computer 160 for on-line display, on-line analysis, and storage. In other embodiments, all data handling is done on an entirely analog basis.

The processor system includes software programs for analyzing the conductance data. Additional software calculates cross-sectional areas based on a number of categories of data, as disclosed herein. However, as discussed in more detail below, to calculate for absolute cross-sectional values, certain errors must be reduced or eliminated. The software can be used to reduce the error in CSA values due to conductance of current in the lumen wall and surrounding tissue and to display the two-dimensional or three-dimensional geometry of the CSA distribution along the length of the vessel (and, optionally, along with the pressure gradient). In one embodiment of the software, a finite element approach or a finite difference approach is used to derive the CSA of organ stenosis, taking parameters such as conductivities of the fluid in the lumen and of the lumen wall and surrounding tissue into consideration.

In another embodiment, simpler circuits are used. As explained herein, absolute cross-sectional values may be calculated based on two or more injections of different NaCl solutions, which varies the conductivity of fluid in the lumen. In other embodiments, the software contains the code for reducing the error in luminal CSA measurement by analyzing signals during interventions, such as infusion of a fluid into the lumen or by changing the amplitude or frequency of the current from the current amplifier. The software chosen for a particular application may allow for computation of the CSA with only a small error instantly or within acceptable time during the medical procedure.

Referring now to FIG. 4A, catheter 22 measures conductance in the body lumen by detecting the change in voltage between detection electrodes 26, 28, as shown by the following equation:

$$\Delta V = \frac{I \cdot L}{C \cdot CSA} \qquad [1a]$$

Thus, the change in voltage, $\Delta V$, is equal to the magnitude of the current, I, multiplied by the distance between the detection electrodes, L, divided by the conductivity of the fluid in the lumen, C, and divided by the cross-sectional area, CSA. Because the current (I), the distance (L), and the conductivity (C) normally can be regarded as calibration constants during a localization procedure, an inversely proportional relationship exists between the voltage difference and the CSA, as shown by the following equation:

$$\Delta V = \frac{I}{CSA} \qquad [1b]$$

In other words, as the cross-sectional area of the lumen decreases, the change in voltage measured by catheter 22 increases. As discussed earlier, conductance and cross-sectional area are proportional. Thus, this equation permits the relative conductances or cross-sectional areas of various intralumen anatomical structures to be determined from measurement of the change in voltage across the lumen using at least one excitation electrode and one detection electrode.

This measurement, however, does not produce accurate, or absolute, values of conductance or cross-sectional area because of the loss of current in the wall of the lumen and surrounding tissue. Although relying on the relative conductances or cross-sectional areas is sufficient for the localization of intraluminal structures, other embodiments for other purposes may require the accurate determination of absolute values for cross-sectional areas.

For example, accurate measures of the luminal cross-sectional area of organ stenosis within acceptable limits enables accurate and scientific stent sizing and placement. Proper stent implantation improves clinical outcomes by avoiding under or over deployment and under or over sizing of a stent, which can cause acute closure or in-stent re-stenosis. In at least one embodiment disclosed herein, an angioplasty or stent balloon includes impedance electrodes supported by the catheter in front of the balloon. These electrodes enable the immediate determination of the cross-sectional area of the vessel during the balloon advancement. This provides a direct measurement of non-stenosed area and allows the selection of the appropriate stent size. In one approach, error due to the loss of current in the wall of the organ and surrounding tissue is corrected by injection of two solutions of NaCl or other solutions with known conductivities. In another embodiment, impedance electrodes are located in the center of the balloon in order to deploy the stent to the desired cross-sectional area. These embodiments and procedures substantially improve the accuracy of stenting and the outcome of such stenting, as well as reduce overall costs.

Other embodiments make diagnosis of valve stenosis more accurate and more scientific by providing a direct, accurate measurement of cross-sectional area of the valve annulus, independent of the flow conditions through the valve. Thus, in such embodiments, the excitation and detection electrodes are embedded within a catheter to measure the valve area directly, independent of cardiac output or pressure drop, and therefore errors in the measurement of valve area are minimized. Further, pressure sensors may be mounted proximal and distal to the impedance electrodes to provide simultaneous pressure gradient recording.

Other embodiments improve evaluation of cross-sectional area and flow in organs like the gastrointestinal tract and the urinary tract At least some of the disclosed embodiments overcome the problems associated with determination of the size (cross-sectional area) of luminal organs, such as, for example, in the coronary arteries, carotid, femoral, renal and iliac arteries, aorta, gastrointestinal tract, urethra, and ureter. In addition, at least some embodiments also provide methods for registration of acute changes in wall conductance, such as, for example, due to edema or acute damage to the tissue, and for detection of muscle spasms/contractions.

The operation of catheter 20, shown in FIG. 4B, is as follows: for electrodes 25, 26, 27, 28, conductance of current flow through the organ lumen and organ wall and surrounding tissue is parallel; i.e., $$G(z, t) = \frac{CSA(z, t) \cdot C_b}{L} + G_p(z, t) \qquad [2a]$$

where $G_p(z,t)$ is the effective conductance of the structure outside the bodily fluid (organ wall and surrounding tissue); $C_b$ is the specific electrical conductivity of the bodily fluid, which for blood generally depends on the temperature, hematocrit, and orientation and deformation of blood cells; and L is the distance between the detection electrodes. This equation shows that conductance, $G(z,t)$, is proportional to the cross-sectional area, CSA $(z,t)$. Thus, a larger conductance will reflect a larger cross-sectional area, and vice versa.

Equation [2a] can be rearranged to solve for cross-sectional area $CSA(z,t)$, with a correction factor, $\alpha$, if the electric field is non-homogeneous, as $$CSA(z, t) = \frac{L}{\alpha C_b}[G(z, t) - G_p(z, t)] \qquad [2b]$$

where α would be equal to 1 if the field were completely homogeneous. The parallel conductance, $G_p$, is an offset error that results from current leakage. $G_p$ would equal 0 if all of the current were confined to the blood and hence would correspond to the cylindrical model given by Equation [1a]. In one approach, finite element analysis is used to properly design the spacing between detection and excitation electrodes relative to the dimensions of the body lumen to provide a nearly homogenous field such that α can be considered equal to 1. Simulations show that a homogenous or substantially homogenous field is provided by (1) the placement of detection electrodes substantially equidistant from the excitation electrodes and (2) maintaining the distance between the detection and excitation electrodes substantially comparable to the body lumen diameter. In one approach, a homogeneous field is achieved by taking steps (1) and/or (2) described above so that α equals 1 in the foregoing analysis.

$G_p$ is a constant at any given position, z, along the long axis of a body lumen, and at any given time, t, in the cardiac cycle. Hence, two injections of different concentrations (and therefore conductivities) of NaCl solution give rise to two equations:

$$C_1 \cdot CSA(z,t) + L \cdot G_p(z,t) = L \cdot G_1(z,t) \quad [3]$$

$$C_2 \cdot CSA(z,t) + L \cdot G_p(z,t) = L \cdot G_2(z,t) \quad [4]$$

which can be solved simultaneously for CSA and $G_p$ as $$CSA(z, t) = L \frac{[G_2(z, t) - G_1(z, t)]}{[C_2 - C_1]} \quad [5]$$

$$G_p(z, t) = \frac{[C_2 \cdot G_1(z, t) - C_1 \cdot G_2(z, t)]}{[C_2 - C_1]} \quad [6]$$

where subscript "1" and subscript "2" designate any two injections of different NaCl concentrations (and conductivities). For each injection k, $C_k$ gives rise to $G_k$ which is measured as the ratio of the root mean square of the current divided by the root mean square of the voltage. The $C_k$ is typically determined through in vitro calibration for the various NaCl concentrations. The concentration of NaCl used is typically on the order of 0.45% to 1.8%. The volume of NaCl solution is typically about 5 ml, but the amount of solution should be sufficient to momentarily displace the entire local vascular blood volume or other body lumen fluid. The values of CSA(t) and $G_p(t)$ can be determined at end-diastole or end-systole (i.e., the minimum and maximum values) or the mean thereof. The value of CSA would vary through the cardiac cycle, but $G_p(t)$ does not vary significantly.

Once the CSA and $G_p$ of the body lumen are determined according to the above embodiment, rearrangement of Equation [2a] allows the calculation of the specific electrical conductivity of bodily fluid in the presence of fluid flow as $$C_b = \frac{L}{CSA(z, t)} [G(z, t) - G_p(z, t)] \quad [7]$$

In this way, Equation [2b] can be used to calculate the CSA continuously (temporal variation, as for example through the cardiac cycle) in the presence of bodily fluid.

In one approach, a pull or push through is used to reconstruct the body lumen CSA along its length. During a long injection of solution (e.g., 10 s to 15 s), the catheter can be pulled back or pushed forward at constant velocity U. Equation [2a] can be expressed as $$CSA(U \cdot t, t) = \frac{L}{C_b} [G(U \cdot t, t) - G_p(U \cdot t, t)] \quad [8]$$

where the axial position, z, is the product of catheter velocity, U, and time, t; i.e., z=U·t.

For the two injections, denoted by subscript "1" and subscript "2", respectively, different time points $T_1$, $T_2$, etc. may be considered such that Equation [8] can be written as $$CSA_1(U \cdot T_1, t) = \frac{L}{C_1} [G_1(U \cdot T_1, t) - G_{p1}(U \cdot T_1, t)] \quad [9a]$$

$$CSA_1(U \cdot T_1, t) = \frac{L}{C_2} [G_2(U \cdot T_1, t) - G_{p1}(U \cdot T_1, t)] \quad [9b]$$

and $$CSA_2(U \cdot T_2, t) = \frac{L}{C_1} [G_1(U \cdot T_2, t) - G_{p2}(U \cdot T_2, t)] \quad [10a]$$

$$CSA_2(U \cdot T_2, t) = \frac{L}{C_2} [G_2(U \cdot T_2, t) - G_{p2}(U \cdot T_2, t)] \quad [10b]$$

and so on. Each set of Equations [9a], [9b] and [10a], [10b], etc., can be solved for $CSA_1$, $G_{p1}$ and $CSA_2$, $G_{p2}$, respectively. Hence, one can measure the CSA at various time intervals and therefore at different positions along the body lumen to reconstruct the length of the lumen. In at least one embodiment, the data on the CSA and parallel conductance as a function of longitudinal position along the body lumen can be exported from an electronic spreadsheet, such as, for example, a Microsoft Excel file, to diagramming software, such as AutoCAD®, where the software uses the coordinates to render a three-dimensional depiction of the lumen on the monitor.

For example, in one approach, the pull back reconstruction was made during a long injection where the catheter was pulled back at constant rate by hand. The catheter was marked along its length such that the pull back was made at 2 mm/sec. Hence, during a 10-second injection, the catheter was pulled back about 2 cm. The data was continuously measured and analyzed at every two second interval; i.e., at every 4 mm. Thus, six different measurements of CSA and $G_p$ were taken which were used to reconstruct the CSA and $G_p$ along the length of the 2 cm segment.

In one approach, the wall thickness is determined from the parallel conductance for those body lumens that are surrounded by air or non-conducting tissue. In such cases, the parallel conductance is equal to $$G_p = \frac{CSA_w \cdot C_w}{L} \quad [11a]$$

where $CSA_w$ is the CSA of the lumen wall and $C_w$ is the electrical conductivity of the wall. This equation can be solved for $CSA_w$ as $$CSA_w = \frac{G_p \cdot L}{C_w} \quad [11b]$$

For a cylindrical body lumen, the wall thickness, h, can be expressed as $$h = \frac{CSA_w}{\pi D} \quad [12]$$

where D is the diameter of the lumen, which can be determined from the circular $CSA (D=[4CSA/\pi]^{1/2})$.

When the CSA, pressure, wall thickness, and flow data are determined according to the embodiments outlined above, it is possible to compute the compliance (e.g., $\Delta CSA/\Delta AP$), tension (e.g., P*r, where P and r are the intraluminal pressure and radius of a cylindrical lumen), stress (e.g., P*r/h, where h is the wall thickness of the cylindrical organ), strain (e.g., $(C-C_d)/C_d$ where C is the inner circumference and $C_d$ is the circumference in diastole), and wall shear stress (e.g., $4\mu Q/r^3$ where $\mu$, Q, and r are the fluid viscosity, flow rate, and radius of the cylindrical lumen for a fully developed flow). These quantities can be used in assessing the mechanical characteristics of the system in health and disease.

In at least one approach for localization or measuring the conductance (and determining the cross-sectional area) of a body lumen, a catheter is introduced from an exteriorly accessible opening (for example, the mouth, nose, or anus for GI applications, or the mouth or nose for airway applications) into the targeted body lumen. For cardiovascular applications, the catheter can be inserted into the lumens in various ways, such as, for example, those used in conventional angioplasty. In at least one embodiment, an 18 gauge needle is inserted into the femoral artery followed by an introducer. A guide wire is then inserted into the introducer and advanced into the lumen of the femoral artery. A 4 or 5 Fr. conductance catheter is then inserted into the femoral artery via wire, and the wire is subsequently retracted. The catheter tip containing the conductance electrodes can then be advanced to the region of interest by use of x-ray (e.g., fluoroscopy). In another approach, this methodology is used on small to medium size vessels (e.g., femoral, coronary, carotid, iliac arteries).

In one approach, a minimum of two injections with different concentrations of NaCl (and, therefore, different conductivities) are required to solve for the two unknowns, CSA and $G_p$. However, in other embodiments disclosed herein, only relative values for conductance or cross-sectional area are necessary, so the injection of two solutions is not necessary. In another approach, three injections will yield three sets of values for CSA and $G_p$ (although not necessarily linearly independent), while four injections would yield six sets of values. In one approach, at least two solutions (e.g., 0.5% and 1.5% NaCl solutions) are injected in the targeted vessel or other lumen. Studies indicate that an infusion rate of approximately 1 ml/s for a five second interval is sufficient to displace the blood volume and results in a local pressure increase of less than 10 mmHg in the coronary artery. This pressure change depends on the injection rate which should be comparable to the lumen flow rate.

In at least one approach, involving the application of Equations [5] and [6], the vessel is under identical or very similar conditions during the two injections. Hence, some variables, such as the infusion rate, bolus temperature, etc., are similar for the two injections. Typically, a short time interval is to be allowed (1 to 2 minute period) between the two injections to permit the vessel to return to homeostatic state. This can be determined from the baseline conductance as shown in FIGS. 7A, 7B, 8A, or 8B. The parallel conductance is preferably the same or very similar during the two injections. Dextran, albumin, or another large molecular weight molecule may be added to the NaCl solutions to maintain the colloid osmotic pressure of the solution to reduce or prevent fluid or ion exchange through the vessel wall.

In one approach, the NaCl solution is heated to body temperature prior to injection since the conductivity of current is temperature dependent. In another approach, the injected bolus is at room temperature, but a temperature correction is made since the conductivity is related to temperature in a linear fashion.

In one approach, a sheath is inserted through either the femoral artery or the carotid artery in the direction of flow. To access the lower anterior descending ("LAD") artery, the sheath is inserted through the ascending aorta. For the carotid artery, where the diameter is typically on the order of 5 mm to 5.5 mm, a catheter having a diameter of 1.9 mm can be used, as determined from finite element analysis, discussed further below. For the femoral and coronary arteries, where the diameter is typically in the range from 3.5 mm to 4 mm, so a catheter of about 0.8 mm diameter would be appropriate. The catheter can be inserted into the femoral, carotid, or LAD artery through a sheath appropriate for the particular treatment. Measurements for all three vessels can be made similarly.

Described here are the protocol and results for one approach that is generally applicable to most arterial vessels. The conductance catheter was inserted through the sheath for a particular vessel of interest. A baseline reading of voltage was continuously recorded. Two containers containing 0.5% and 1.5% NaCl were placed in temperature bath and maintained at 37° C. A 5 ml to 10 ml injection of 1.5% NaCl was made over a 5 second interval. The detection voltage was continuously recorded over a 10 second interval during the 5 second injection. Several minutes later, a similar volume of 1.5% NaCl solution was injected at a similar rate. The data was again recorded. Matlab® was used to analyze the data including filtering with high pass and with low cut off frequency (1200 Hz). The data was displayed using Matlab®, and the mean of the voltage signal during the passage of each respective solution was recorded. The corresponding currents were also measured to yield the conductance (G=I/V). The conductivity of each solution was calibrated with six different tubes of known CSA at body temperature. A model using Equation [1a] was fitted to the data to calculate conductivity C. The analysis was carried out with SPSS statistical software using the non-linear regression fit. Given C and G for each of the two injections, an Excel spreadsheet file was formatted to calculate the CSA and $G_p$ as per equations [5] and [6], respectively. These measurements were repeated several times to determine the reproducibility of the technique. The reproducibility of the data was within 5%. Ultrasound was used to measure the diameter of the vessel simultaneous with our conductance measurements. The detection electrodes were visualized with ultrasound, and the diameter measurements was made at the center of the detection electrodes. The maximum differences between the conductance and ultrasound measurements were within 10%.

FIGS. 7A, 7B, 8A, and 8B illustrate voltage measurements in the blood stream in the left carotid artery. Here, the data acquisition had a sampling frequency of 75 KHz, with two channels—the current injected and the detected voltage, respectively. The current injected has a frequency of 5 KHz, so the voltage detected, modulated in amplitude by the impedance changing through the bolus injection, will have a spectrum in the vicinity of 5 KHz.

Figure 7A:
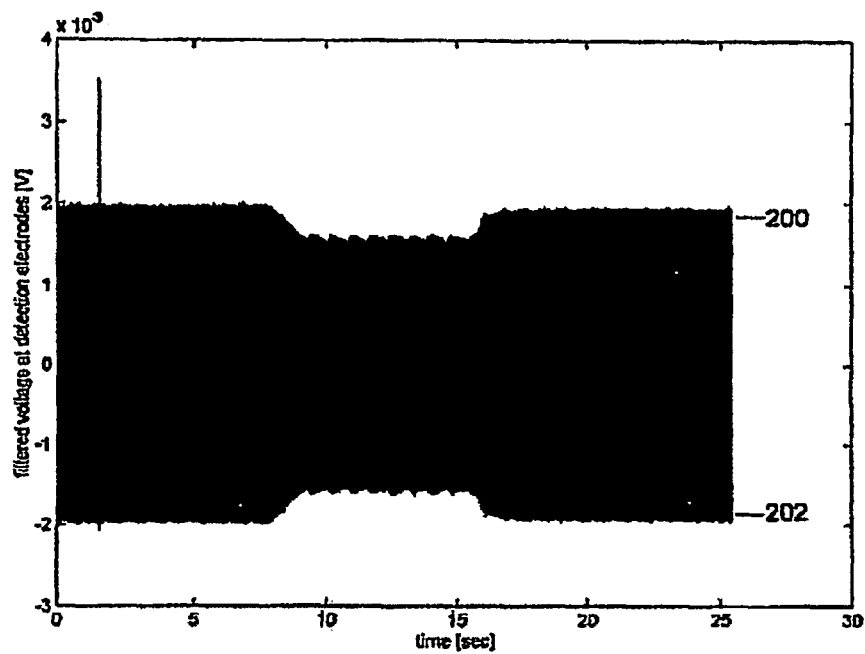
FIG. 7A shows the detected filtered voltage drop as measured in the blood stream before and after injection of 1.5% NaCl solution.
Figure 7B:
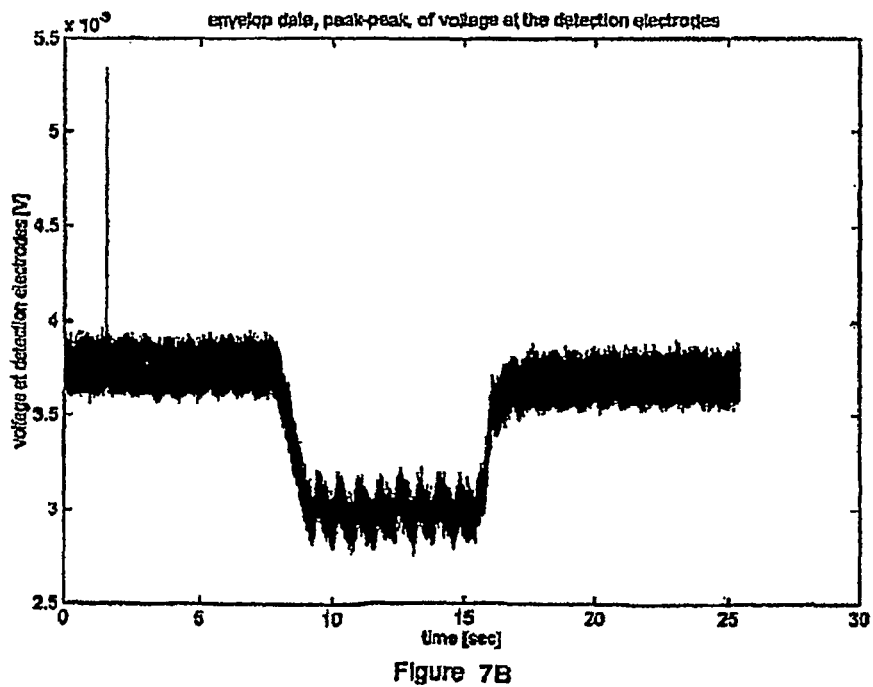
FIG. 7B shows the peak-to-peak envelope of the detected voltage shown in FIG. 7A.
Figure 8A:
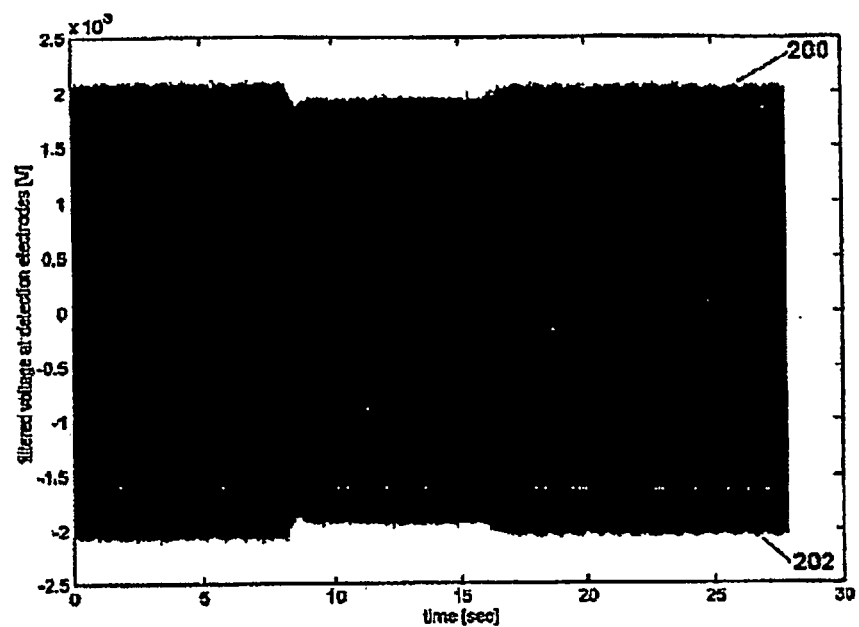
FIG. 8A shows the detected filtered voltage drop as measured in the blood stream before and after injection of 0.5% NaCl solution.
Figure 8B:
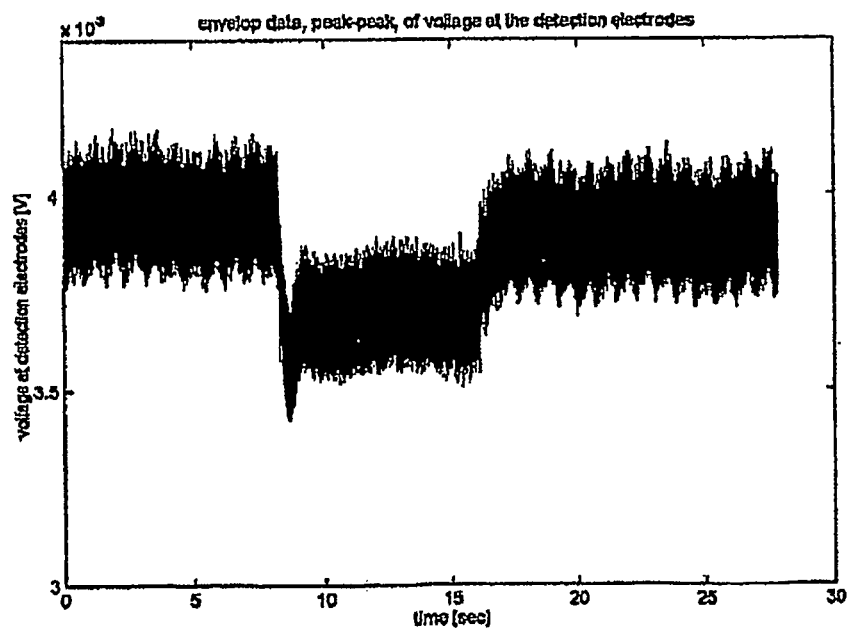
FIG. 8B shows the peak-to-peak envelope of the detected voltage shown in FIG. 8A.

With reference to FIG. 7A there is shown a signal processed with a high pass filter with low cut off frequency (1200 Hz). The top and bottom portions 200, 202 show the peak-to-peak envelope detected voltage which is displayed in FIG. 7B. The initial 7 seconds correspond to the baseline; i.e., electrodes in the blood stream. The next 7 seconds correspond to an injection of hyper-osmotic NaCl solution (1.5% NaCl). It can be seen that the voltage is decreased, implying increased conductance (since the injected current is constant). Once the NaCl solution is washed out, the baseline is recovered as shown in FIGS. 7A and 7B. FIGS. 8A and 8B show similar data corresponding to 0.5% NaCl solutions.

The voltage signals are ideal since the difference between the baseline and the injected solution is apparent and systematic. Furthermore, the pulsation of vessel diameter can be seen in the 0.5% and 1.5% NaCl injections (FIGS. 7A, 7B and 8A, 8B, respectively). This allows determination of the variation of CSA throughout the cardiac cycle as outline above.

The NaCl solution can be injected by hand or by using a mechanical injector to momentarily displace the entire volume of blood or bodily fluid in the lumen segment of interest. For example, in a blood vessel, the pressure generated by the injection will not only displace the blood in the antegrade direction (in the direction of blood flow) but also in the retrograde direction (by momentarily pushing the blood backwards). In other visceral organs which may be normally collapsed, the NaCl solution will not displace blood as in the vessels but will merely open the organs and create a flow of the fluid. In one approach, after injection of a first solution into the treatment or measurement site, sensors monitor and confirm baseline of conductance prior to injection of a second solution into the treatment site.

The injections described above are preferably repeated at least once to reduce errors associated with the administration of the injections, such as, for example, where the injection does not completely displace the blood or where there is significant mixing with blood. It will be understood that any bifurcation(s) (with branching angle near 90 degrees) near the targeted lumen can cause an overestimation of the calculated CSA. Hence, generally the catheter should be slightly retracted or advanced and the measurement repeated. An additional application with multiple detection electrodes or a pull back or push forward during injection will accomplish the same goal. Here, an array of detection electrodes can be used to minimize or eliminate errors that would result from bifurcations or branching in the measurement or treatment site.

In one approach, error due to the eccentric position of the electrode or other imaging device can be reduced by inflation of a balloon on the catheter. The inflation of the balloon during measurement will place the electrodes or other imaging device in the center of the vessel away from the wall. In the case of impedance electrodes, the inflation of the balloon can be synchronized with the injection of a bolus such that the balloon inflation would immediately precede the bolus injection. Our results, however, show that the error due to catheter eccentricity is small.

The CSA predicted by Equation [5] corresponds to the area of the vessel or other lumen external to the catheter (i.e., CSA of vessel minus CSA of catheter). If the conductivity of the NaCl solutions is determined by calibration from Equation [1a] with various tubes of known CSA, then the calibration accounts for the dimension of the catheter and the calculated CSA corresponds to that of the total vessel lumen. In at least one embodiment, the calibration of the CSA measurement system will be performed at 37° C. by applying 100 mmHg in a solid polyphenolenoxide block with holes of known CSA ranging from 7.065 mm$^2$ (3 mm in diameter) to 1017 mm$^2$ (36 mm in diameter). If the conductivity of the solutions is obtained from a conductivity meter independent of the catheter, however, then the CSA of the catheter is generally added to the CSA computed from Equation [5] to give the total CSA of the vessel.

The signals are generally non-stationary, nonlinear, and stochastic. To deal with non-stationary stochastic functions, one can use a number of methods, such as the Spectrogram, the Wavelet's analysis, the Wigner-Ville distribution, the Evolutionary Spectrum, Modal analysis, or the intrinsic model function ("IMF") method. The mean or peak-to-peak values can be systematically determined by the aforementioned signal analysis and used in Equation [5] to compute the CSA.

For the determination of conductance or cross-sectional area of a heart valve, it is generally not feasible to displace the entire volume of the heart. Hence, the conductivity of the blood is transiently changed by injection of a hypertonic NaCl solution into the pulmonary artery. If the measured total conductance is plotted versus blood conductivity on a graph, the extrapolated conductance at zero conductivity corresponds to the parallel conductance. In order to ensure that the two inner electrodes are positioned in the plane of the valve annulus (2 mm to 3 mm), in one embodiment, two pressure sensors 36 are placed immediately proximal and distal to (1 mm to 2 mm above and below, respectively) the detection electrodes or sets of detection electrodes (see, e.g., FIGS. 4A and 4F). The pressure readings will then indicate the position of the detection electrode relative to the desired site of measurement (aortic valve: aortic-ventricular pressure; mitral valve: left ventricular-atrial pressure; tricuspid valve: right atrial-ventricular pressure; pulmonary valve: right ventricular-pulmonary pressure). The parallel conductance at the site of annulus is generally expected to be small since the annulus consists primarily of collagen, which has low electrical conductivity. In another application, a pull back or push forward through the heart chamber will show different conductance due to the change in geometry and parallel conductance. This can be established for normal patients, which can then be used to diagnose valvular stenosis.

In one approach, for the esophagus or the urethra, the procedures can conveniently be done by swallowing fluids of known conductivities into the esophagus and infusion of fluids of known conductances into the urinary bladder followed by voiding the volume. In another approach, fluids can be swallowed or urine voided followed by measurement of the fluid conductivities from samples of the fluid. The latter method can be applied to the ureter where a catheter can be advanced up into the ureter and fluids can be injected from a proximal port on the probe (will also be applicable in the intestines) or urine production can be increased and samples taken distal in the ureter during passage of the bolus or from the urinary bladder.

In one approach, concomitant with measuring the conductance, cross-sectional area, and/or pressure gradient at the treatment or measurement site, a mechanical stimulus is introduced by way of inflating the balloon or by releasing a stent from the catheter, thereby facilitating flow through the stenosed part of the lumen. In another approach, concomitant with measuring the conductance, cross-sectional area, and/or pressure gradient at the treatment site, one or more pharmaceutical substances for diagnosis or treatment of stenosis is injected into the treatment site. For example, in one approach, the injected substance can be a smooth muscle agonist or antagonist. In yet another approach, concomitant with measuring the conductance, cross-sectional area, and/or pressure gradient at the treatment site, an inflating fluid is released into the treatment site for release of any stenosis or materials causing stenosis in the lumen or treatment site.

Again, it will be noted that the methods, systems, and catheters described herein can be applied to any body lumen or treatment site. For example, the methods, systems, and catheters described herein can be applied to any one of the following hollow bodily systems: the cardiovascular system including the heart; the digestive system; the respiratory system; the reproductive system; and the urogenital tract.

Finite Element Analysis: In one preferred approach, finite element analysis (FEA) is used to verify the validity of Equations [5] and [6]. There are two major considerations for the model definition: geometry and electrical properties. The general equation governing the electric scalar potential distribution, V, is given by Poisson's equation as:

$$\nabla \cdot (CVV) = -1 \quad [13]$$

where C, I and $\nabla$ are the conductivity, the driving current density, and the del operator, respectively. Femlab or any standard finite element package can be used to compute the nodal voltages using Equation [13]. Once V has been determined, the electric field can be obtained from $E=-\nabla V$.

The FEA allows the determination of the nature of the field and its alteration in response to different electrode distances, distances between driving electrodes, wall thicknesses, and wall conductivities. The percentage of total current in the lumen of the vessel (% I) can be used as an index of both leakage and field homogeneity. Hence, the various geometric and electrical material properties can be varied to obtain the optimum design, i.e., minimizing the non-homogeneity of the field. Furthermore, the experimental procedure was simulated by injection of the two solutions of NaCl to verify the accuracy of Equation [5]. Finally, the effect of the presence of electrodes and the catheter in the lumen of vessel was assessed. The error terms representing the changes in measured conductance due to the attraction of the field to the electrodes and the repulsion of the field from the resistive catheter body were quantified.

Poisson's equation was solved for the potential field, which takes into account the magnitude of the applied current, the location of the current driving and detection electrodes, and the conductivities and geometrical shapes in the model including the vessel wall and surrounding tissue. This analysis suggests that the following conditions are optimal for the cylindrical model: (1) the placement of detection (voltage sensing) electrodes equidistant from the excitation (current driving) electrodes; (2) the distance between the excitation electrodes should be much greater than the distance between the detection electrodes; and (3) the distance between the detection and excitation electrodes is comparable to the vessel diameter, or the diameter of the vessel is small relative to the distance between the driving electrodes. If these conditions are satisfied, the equipotential contours more closely resemble straight lines perpendicular to the axis of the catheter and the voltage drop measured at the wall will be nearly identical to that at the center. Since the curvature of the equipotential contours is inversely related to the homogeneity of the electric field, it is possible to optimize the design to minimize the curvature of the field lines. Consequently, in one approach, one or more of conditions (1)-(3) described above are met to increase the accuracy of the cylindrical model.

Theoretically, it is impossible to ensure a completely homogeneous field given the current leakage through the lumen wall into the surrounding tissue. It was found that the iso-potential line is not constant as one moves out radially along the vessel as stipulated by the cylindrical model. FIGS. 11A and 11B show the detected voltage for a catheter with a radius of 0.55 mm for two different NaCl solutions (0.5% and 1.5%, respectively). The origin corresponds to the center of the catheter. The first vertical line 220 represents the inner part of the electrode which is wrapped around the catheter, and the second vertical line 221 is the outer part of the electrode in contact with the solution (diameter of electrode is approximately 0.25 mm). The six different curves, top to bottom, correspond to six different vessels with radii of 3.1 mm, 2.7 mm, 2.3 mm, 1.9 mm, 1.5 mm, and 0.55 mm, respectively. It can be seen that a "hill" 220, 221 occurs at the detection electrodes, followed by a fairly uniform plateau in the vessel lumen, followed by an exponential decay into the surrounding tissue. Since the potential difference is measured at the detection electrode 220, 221, the simulation generates the "hill" whose value corresponds to the equivalent potential in the vessel as used in Equation [5]. Thus, for each catheter size, the dimension of the vessel was varied such that Equation [5] was exactly satisfied. Consequently, the optimum catheter size for a given vessel diameter was obtained such that the distributive model satisfies the lumped equations (Equations [5] and [6]). In this way, a relationship between vessel diameter and catheter diameter can be generated such that the error in the CSA determination is less than 5%. In one embodiment, different diameter catheters are prepackaged and labeled for optimal use in certain size vessel. For example, for vessel dimensions in the range of 4 mm to 5 mm, 5 mm to 7 mm, or 7 mm to 10 mm, analysis shows that optimum diameter catheters will be in the range of 0.9 mm to 1.4 mm, 1.4 mm to 2 mm, or 2 mm to 4.6 mm, respectively. The clinician can select the appropriate diameter catheter based on the estimated vessel diameter of interest. This decision will be made prior to the procedure and will serve to minimize the error in the determination of lumen CSA.

Thus, a number of the embodiments disclosed herein accurately calculate lumen cross-sectional area by measuring conductance and correcting for various errors inherent in such measurements. However, at least some of the disclosed embodiments provide for the localization of body lumen junctions and other intraluminal anatomical structures using relative conductances and/or cross-sectional areas. Because only relative differences in conductance or cross-sectional area are necessary for accurate localization, the calculation of absolute values for various locations within the body lumen may be skipped in most instances.

While various embodiments of devices, systems, and methods for localization of body lumen junctures have been described in considerable detail herein, the embodiments are merely offered by way of non-limiting examples of the invention described herein. Many variations and modifications of the embodiments described herein will be apparent to one of ordinary skill in the art in light of the this disclosure. It will therefore be understood by those skilled in the art that various changes and modifications may be made, and equivalents may be substituted for elements thereof, without departing from the scope of the invention. Indeed, this disclosure is not intended to be exhaustive or to limit the scope of the invention. The scope of the invention is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present invention.

It is therefore intended that the invention will include, and this description and the appended claims will encompass, all modifications and changes apparent to those of ordinary skill in the art based on this disclosure.

I claim:

1. A system, comprising:
a device having a proximal end and a distal end, the distal end of the device for placement into a body lumen, the device comprising a first pair of excitation electrodes configured to emit a charge and a first pair of detection electrodes configured to obtain conductance data indicative of a change in voltage of the charge at a plurality of locations over a distance within the body lumen, the conductance data indicative of identified changes in relative cross-sectional areas at each of the plurality of locations, the conductance data obtained at each of the plurality of locations when both the first pair of excitation electrodes and the first pair of detection electrodes are immersed in a fluid within the body lumen, wherein the change in voltage is inversely proportional to a cross-sectional area of the body lumen, and
wherein a processor connected to the first pair of detection electrodes of the device is configured to generate a profile of the body lumen from the conductance data, the profile depicting the conductance data at each of the plurality of locations, wherein the relative cross-sectional areas can be calculated by the processor for each of the plurality of locations within the body lumen using an equation $\Delta V=I/CSA$ such that a junction between two lumina can be identified within the profile through a change in relative conductance between at least two locations of the plurality of locations and wherein the identification of the junction between two lumina is used for localizing the device in the body lumen in relation to a target tissue for ablation;
wherein $\Delta V$ is equivalent to the change in voltage at a location, I is equivalent to a magnitude of the charge detected by the first pair of detection electrodes, and CSA is equivalent to the cross-sectional area of the body lumen at the location; and
wherein a distance between the first pair of excitation electrodes and the first pair of detection electrodes is comparable to a vessel diameter.

2. The system of claim 1, wherein:
the body lumen comprises a lumen selected from the group consisting of at least a portion of an atrium, a pulmonary vein-atrial junction, a blood vessel, a biliary tract, and an esophagus; and
wherein the distance between the first pair of excitation electrodes and the first pair of detection electrodes is determined using finite element analysis.

3. The system of claim 1, wherein:
the fluid comprises blood.

4. The system of claim 1, wherein:
the processor is further capable of calculating an absolute cross-sectional area of the body lumen at each of the plurality of locations within the body lumen using conductance data obtained by operation of the first pair of excitation electrodes and the first pair of detection electrodes.

5. The system of claim 4, wherein:
the device further comprises a passageway for passing fluid through the device to the location of the first pair of detection electrodes, such that fluid passing through the passageway comes in contact with the first pair of detection electrodes;
the fluid within the body lumen comprises a first fluid having a first conductivity and a second fluid having a second conductivity; and
the conductance data is determined at each of the plurality of locations when both the first set of excitation electrodes and the first set of detection electrodes are immersed in each of the first fluid and the second fluid.

6. The system of claim 5, wherein:
the conductance data comprises a first conductance value determined at each of the plurality of locations when both the first set of excitation electrodes and the first set of detection electrodes are immersed in the first fluid and a second conductance value determined at each of the plurality of locations when both the first set of excitation electrodes and the first set of detection electrodes are immersed in the second fluid.

7. The system of claim 6, wherein:
the profile of the body lumen is determined from the first and second conductance values collected from each of the plurality of locations, the first conductivity of the first fluid, and the second conductivity of the second fluid.

8. The system of claim 1, wherein:
the first pair of detection electrodes are located between the first pair of excitation electrodes; and
the device further comprises a balloon positioned proximal to the first pair of excitation electrodes and the first pair of detection electrodes, the balloon configured for inflation and deflation.

9. The system of claim 1, wherein:
the device further comprises at least one ablation contact positioned at the distal end of the device, the at least one ablation contact being configured to remove or destroy a targeted tissue within the body lumen.

10. The system of claim 9, wherein:
the targeted tissue comprises tissue located at or adjacent to a pulmonary vein-atrial junction.

11. The system of claim 9, wherein:
the targeted tissue at least partially surrounds the pulmonary vein-atrial junction.

12. The system of claim 9, wherein:
the targeted tissue substantially surrounds the pulmonary vein-atrial junction.

13. The system of claim 9, wherein:
the at least one ablation contact comprises a heating element such that the at least one ablation contact is capable of transferring heat to the targeted tissue.

14. The system of claim 9, wherein:
the at least one ablation contact is positioned circumferentially around a substantially circular portion of the device.

15. The system of claim 9, wherein:
the at least one ablation contact is configured to remove or destroy the targeted tissue by cryoablation.

16. The system of claim 9, wherein:
the at least one ablation contact is configured to remove or destroy the targeted tissue by delivering an electrical current to the targeted tissue.

17. The system of claim 16, further comprising:
a grounding electrode configured to be placed on the body such that the electrical current flows from the targeted tissue to the grounding electrode.

18. The system of claim 17, wherein:
the grounding electrode comprises an adhesive for removably connecting the grounding electrode to the body.

19. A system for ablating a targeted tissue, comprising:
a device having a proximal end and a distal end, the distal end of the device for placement into a body lumen, the device comprising
two excitation electrodes configured to emit a charge and at least two detection electrodes, and
at least one ablation contact positioned at the distal end of the device, the at least one ablation contact being configured to remove or destroy a targeted tissue within the body lumen;
wherein the at least two detection electrodes of the device are configured to obtain conductance data indicative of a change in voltage of the charge at a plurality of locations over a distance within the body lumen, the conductance data indicative of identified changes in relative cross-sectional areas at each of the plurality of locations, the conductance data obtained at each of the plurality of locations when the two excitation electrodes and at least two detection electrodes are immersed in a fluid within the body lumen, wherein the change in voltage is inversely proportional to a cross-sectional area of the body lumen; and
a processor connected to the two excitation electrodes and the at least two detection electrodes of the device, the processor configured to generate a profile of the body lumen from the conductance data, the profile depicting the conductance data at each of the plurality of locations, wherein the relative cross-sectional areas can be calculated by the processor for each of at the plurality of locations within the body lumen using an equation $\Delta V = I/CSA$ such that a junction between two lumina can be identified within the profile through a change in relative conductance between at least two locations of the plurality of locations and wherein the identification of the junction between two lumina is used for localizing the device in the body lumen in relation to a target tissue for ablation;
wherein $\Delta V$ is equivalent to the change in voltage at a location, I is equivalent to a magnitude of the charge detected by the first pair of detection electrodes, and CSA is equivalent to the relative cross-sectional area of the body lumen at the location; and
wherein a distance between the excitation electrodes and detection electrodes is comparable to the body lumen diameter.

20. The system of claim 19, wherein:
the body lumen comprises a lumen selected from the group consisting of at least a portion of an atrium, a pulmonary vein-atrial junction, a blood vessel, a biliary tract, and an esophagus.

21. The system of claim 19, wherein:
the fluid comprises blood.

22. The system of claim 19, wherein:
the processor is further capable of calculating an absolute cross-sectional area of the body lumen at each of the plurality of locations within the body lumen using conductance data obtained by operation of the at least two excitation electrodes and the at least two detection electrodes.

23. The system of claim 22, wherein:
the device further comprises a passageway for passing fluid through the device to the location of the insert two excitation electrodes and the at least two detection electrodes, such that fluid passing through the passageway comes in contact with the two excitation electrodes and the at least two detection electrodes;
the fluid within the body lumen comprises a first fluid having a first conductivity and a second fluid having a second conductivity; and
the conductance data is determined at each of the plurality of locations when the two excitation electrodes and the at least two detection electrodes are immersed in each of the first fluid and the second fluid.

24. The system of claim 23, wherein:
the fluid further comprises a first fluid having a first conductivity and a second fluid having a second conductivity; and
the conductance data comprises a first conductance value determined at each of the plurality of locations when the two excitation electrodes and the at least two detection electrodes are immersed in the first fluid and a second conductance value determined at each of the plurality of locations when the two excitation electrodes and the at least two detection electrodes are immersed in the second fluid.

25. The system of claim 24, wherein:
the profile of the body lumen is determined from the first and second conductance values collected from each of the plurality of locations, the first conductivity of the first fluid, and the second conductivity of the second fluid.

26. The system of claim 19, wherein:
the at least two detection electrodes are located between the two excitation electrodes.

27. The system of claim 19, wherein:
the targeted tissue comprises tissue located at or adjacent to a pulmonary vein-atrial junction.

28. The system of claim 19, wherein:
the targeted tissue at least partially surrounds the pulmonary vein-atrial junction.

29. The system of claim 19, wherein:
the targeted tissue substantially surrounds the pulmonary vein-atrial junction.

30. The system of claim 19, wherein:
the at least one ablation contact comprises a heating element such that the at least one ablation contact is capable of transferring heat to the targeted tissue.

31. The system of claim 19, wherein:
the at least one ablation contact is positioned circumferentially around a substantially circular portion of the device.

32. The system of claim 31, wherein:
the at least one ablation contact comprises a plurality of ablation contacts positioned circumferentially around a substantially circular portion of the device.

33. The system of claim 19, wherein:
the at least one ablation contact is configured to remove or destroy the targeted tissue by cryoablation.

34. The system of claim 19, wherein:
the at least one ablation contact is configured to remove or destroy the targeted tissue by delivering an electrical current to the targeted tissue.

35. The system of claim 34, further comprising:
a grounding electrode configured to be placed on the body such that the electrical current flows from the targeted tissue to the grounding electrode.

36. The system of claim 35, wherein:
the grounding electrode comprises an adhesive for removably connecting the grounding electrode to the body.

37. A system, comprising:
a device having a proximal end and a distal end, the distal end of the device for placement into a body lumen, the device comprising at least one pair of excitation electrodes configured to emit a charge and at least one pair of detection electrodes configured to obtain conductance data indicative of a change in voltage of the charge at a plurality of locations over a distance within the body lumen, the conductance data indicative of identified changes in relative cross-sectional areas at each of the plurality of locations, the conductance data obtained at each of the plurality of locations when the at least one pair of excitation electrodes and the at least one pair of detection electrodes are immersed in a fluid within the body lumen, wherein the change in voltage is inversely proportional to a cross-sectional area of the body lumen; and
wherein a processor connected to each of the pairs of excitation and detection electrodes of the device is configured to generate a conductance profile of the body lumen using the conductance data, the profile depicting the conductance data at each of the plurality of locations, wherein the relative cross-sectional areas can be calculated by the processor for each of the plurality of locations within the body lumen using an equation $\Delta V = I/CSA$ such that a junction between two lumina can be identified within the profile through a change in relative conductance between at least two locations of the plurality of locations and wherein the identification of the junction between two lumina is used for localizing the device in the body lumen in relation to a target tissue for ablation;
wherein $\Delta V$ is equivalent to the change in voltage at a location, I is equivalent to a magnitude of the charge detected by the first pair of detection electrodes, and CSA is equivalent to the relative cross-sectional area of the body lumen at the location; and
wherein a distance between the at least one pair of excitation electrodes and the at least one pair of detection electrodes is comparable to the body lumen diameter.

38. The system of claim 37, wherein:
the processor is further capable of using conductance data obtained by operation of the at least one pair of excitation electrodes and the at least one pair of detection electrodes to calculate an absolute cross-sectional area of the body lumen at each of the plurality of locations within the body lumen.

39. The system of claim 37, wherein:
the device further comprises at least one ablation contact positioned at the distal end of the device, the at least one ablation contact being configured to remove or destroy a targeted tissue within the body lumen.

40. The system of claim 39, wherein:
the targeted tissue comprises tissue located at or adjacent to a pulmonary vein-atrial junction.

41. The system of claim 39, wherein:
the targeted tissue at least partially surrounds the pulmonary vein-atrial junction.

42. The system of claim 39, wherein:
the targeted tissue substantially surrounds the pulmonary vein-atrial junction.

43. The system of claim 39, wherein:
the at least one ablation contact comprises a heating element such that the at least one ablation contact is capable of transferring heat to the targeted tissue.

44. The system of claim 39, wherein:
the at least one ablation contact is positioned circumferentially around a substantially circular portion of the device.

45. The system of claim 39, wherein:
the at least one ablation contact is configured to remove or destroy the targeted tissue by cryoablation.

46. The system of claim 39, wherein:
the at least one ablation contact is configured to remove or destroy the targeted tissue by delivering an electrical current to the targeted tissue.

47. The system of claim 46, further comprising:
a grounding electrode configured to be placed on the body such that the electrical current flows from the targeted tissue to the grounding electrode.

48. The system of claim 47, wherein:
the grounding electrode comprises an adhesive for removably connecting the grounding electrode to the body.

49. A system for ablation of a targeted tissue, comprising:
a device having a proximal end and a distal end, the distal end of the device for placement into a body lumen, the device comprising
at least one pair of excitation electrodes configured to emit a charge and at least one pair of detection electrodes, and
at least one ablation contact positioned at the distal end of the device, the at least one ablation contact being configured to remove or destroy a targeted tissue within the body lumen;
wherein the at least one pair of detection electrodes of the device is configured to obtain conductance data indicative of a change in voltage of the charge at a plurality of locations over a distance within the body lumen, the conductance data indicative of identified changes in relative cross-sectional areas at each of the plurality of locations, the conductance data obtained at each of the plurality of locations when the at least one pair of excitation electrodes and the at least one pair of detection electrodes are immersed in a fluid within the body lumen, wherein the change in voltage is proportional to a cross-sectional area of the body lumen;
a processor connected to the at least one pair of excitation electrodes and the at least one detection pair of electrodes, the processor configured to generate a profile of the body lumen from the conductance data, the profile depicting the conductance data at each of the plurality of locations, wherein the relative cross-sectional areas can be calculated by the processor for each of the plurality of locations within the body lumen using an equation ΔV=I/CSA such that a junction between two lumina can be identified within the profile through a change in relative conductance between at least two locations of the plurality of locations and wherein the identification of the junction between two lumina is used for localizing the device in the body lumen in relation to a target tissue for ablation;

wherein ΔV is equivalent to the change in voltage at a location, I is equivalent to a magnitude of the charge detected by the first pair of detection electrodes, and CSA is equivalent to the relative cross-sectional area of the body lumen at the location; and wherein a distance between the at least one pair of excitation electrodes and the at least one pair of detection electrodes is comparable to the body lumen diameter.

50. The system of claim 49, wherein:
the processor is further capable of calculating an absolute cross-sectional area at each of the plurality of locations in the body lumen using conductance data obtained by operation of the at least one pair of excitation electrodes and the at least one pair of detection electrodes.

51. The system of claim 49, wherein:
the targeted tissue comprises tissue located at or adjacent to a pulmonary vein-atrial junction.

52. The system of claim 49, wherein:
the targeted tissue at least partially surrounds the pulmonary vein-atrial junction.

53. The system of claim 49, wherein:
the targeted tissue substantially surrounds the pulmonary vein-atrial junction.

54. The system of claim 49, wherein:
the at least one ablation contact comprises a heating element such that the at least one ablation contact is capable of transferring heat to the targeted tissue.

55. The system of claim 49, wherein:
the at least one ablation contact is positioned circumferentially around a substantially circular portion of the device.

56. The system of claim 49, wherein:
the at least one ablation contact is configured to remove or destroy the targeted tissue by cryoablation.

57. The system of claim 49, wherein:
the at least one ablation contact is configured to remove or destroy the targeted tissue by delivering an electrical current to the targeted tissue.

58. The system of claim 57, further comprising:
a grounding electrode configured to be placed externally on the body such that the electrical current flows from the targeted tissue to the grounding electrode.

59. The system of claim 58, wherein:
the grounding electrode comprises an adhesive for removably connecting the grounding electrode to the body.

60. The system of claim 49, wherein:
the at least one pair of detection electrodes are positioned on the device between the at least one pair of excitation electrodes.

61. A method for localizing a junction or other structure within a body lumen, comprising the steps of:
introducing at least part of a system into a body lumen, the system comprising:
a device having a proximal end and a distal end, the distal end of the device for placement into a body lumen, the device comprising a first pair of excitation electrodes configured to emit electrical current flow and a first pair of detection electrodes configured to obtain conductance data indicative of a change in voltage of the electrical current flow at a plurality of locations over a distance within the body lumen, the conductance data indicative of identified changes in relative cross-sectional areas at each of the plurality of locations, the conductance data obtained at each of the plurality of locations when the first pair of excitation and the first pair of detection electrodes are immersed in a fluid within the body lumen, wherein the change in voltage is inversely proportional to a cross-sectional area of the body lumen;

wherein a distance between the first pair of excitation electrodes and the first pair of detection electrodes is comparable to the body lumen diameter; and a processor connected to the first pair of detection electrodes of the device, the processor configured to generate a profile of the body lumen from the conductance data, the profile depicting the conductance data at each of the plurality of locations, wherein the relative cross-sectional areas can be calculated by the processor for each of the plurality of locations within the body lumen using an equation ΔV=I/CSA such that a junction between two lumina can be identified within the profile through a change in relative conductance between at least two locations of the plurality of locations and wherein the identification of the junction between two lumina is used for localizing the device in the body lumen in relation to a target tissue for ablation;

wherein ΔV is equivalent to the change in voltage at a location, I is equivalent to a magnitude of the electrical current flow detected by the first pair of detection electrodes, and CSA is equivalent to the relative cross-sectional area of the body lumen at the location;

providing electrical current flow to the body lumen through the device;

measuring a first conductance value at a first location in the body lumen;

moving the device to a second location in the body lumen;

measuring a second conductance value at a second location in the body lumen; and determining the profile of the body lumen based on the first conductance value of the first location and the second conductance value of the second location.

62. The method of claim 61, wherein:
the body lumen comprises a blood vessel; and
the fluid comprises blood.

63. The system of claim 61, wherein:
the body lumen comprises a lumen selected from the group consisting of at least a portion of an atrium, a biliary tract, and an esophagus.

64. The method of claim 61, wherein:
the device further comprises a passageway for passing fluid through the device to the location of the first pair of detection electrodes, such that fluid passing through the passageway comes in contact with the first pair of detection electrodes;
the fluid within the body lumen comprises a first fluid having a first conductivity and a second fluid having a second conductivity; and
the conductance data is determined at each of the plurality of locations when the first pairs of excitation and detection electrodes are immersed in each of the first fluid and the second fluid.

65. The method of claim 64, further comprising:
injecting a first solution having a first conductivity into the body lumen;

injecting a second solution having a second conductivity into the body lumen, wherein the second conductivity does not equal the first conductivity;

measuring a second conductance value at the first location in the body lumen;

calculating the conductance data at the first location in the body lumen;

measuring a first conductance value at a second location in the body lumen; and calculating the conductance data at the second location in the body lumen.

66. The method of claim 65, wherein:

the step of determining a profile of the body lumen comprises determining a profile of the body lumen based on the conductance of the first location, the conductance data of the first location, the conductance data of the second location, and the conductivities of the first and second solutions.

67. The method of claim 61, wherein:

the first pair of detection electrodes are located between the first pair of detection electrodes.

68. A method for ablating a targeted tissue, comprising the steps of:

introducing at least part of a system into a body lumen, the system comprising:

a device having a proximal end and a distal end, the distal end of the device for placement into a body lumen, the device comprising:

at least one pair of excitation electrodes configured to emit a charge and at least one pair of detection electrodes, wherein a distance between the at least one pair of excitation electrodes and the at least one pair of detection electrodes is comparable to the body lumen diameter, at least one ablation contact positioned at the distal end of the device, the at least one ablation contact being configured to remove or destroy a targeted tissue within the body lumen;

wherein the at least one pair of detection electrodes of the device is configured to obtain conductance data indicative of a change in voltage at a plurality of locations over a distance within the body lumen, the conductance data indicative of identified changes in relative cross-sectional areas at each of the plurality of locations, the conductance data obtained at each of the plurality of locations when the at least one pair of excitation electrodes and the at least one pair of detection electrodes are immersed in a fluid within the body lumen, wherein the change in voltage is proportional to a cross-sectional area of the body lumen; and a processor connected to the at least one pair of excitation electrodes and the at least one pair of detection electrodes of the device, the processor configured to generate a profile of the body lumen from the conductance data, the profile depicting the conductance data at each of the plurality of locations, wherein the relative cross-sectional areas can be calculated by the processor for each of the plurality of locations within the body lumen using an equation $\Delta V = I/CSA$ such that a junction between two lumina can be identified within the profile through a change in relative conductance between at least two locations of the plurality of locations and wherein the identification of the junction between two lumina is used for localizing the device in the body lumen in relation to a target tissue for ablation;

wherein $\Delta V$ is equivalent to the change in voltage at a location, I is equivalent to a magnitude of the charge detected by the first pair of detection electrodes, and CSA is equivalent to the relative cross-sectional area of the body lumen at the location;

providing electrical current flow to the body lumen through the device;

measuring a first conductance value at a first location in the body lumen;

moving the device to a second location in the body lumen;

measuring a second conductance value at a second location in the body lumen;

determining a profile of the body lumen based on the first conductance value of the first location and the second conductance value of the second location;

using the profile to locate the device in the body lumen in relation to the targeted tissue; and ablating the targeted tissue using the device.

69. The method of claim 68, wherein the profile comprises conductances.

70. The method of claim 68, wherein:

the at least one pair of detection electrodes are located between the at least one pair of excitation electrodes.

71. The system of claim 1, wherein the device is selected from the group consisting of a wire and a catheter.

72. The system of claim 1, wherein the device comprises a wire inserted through a guide catheter, where the infusion of a bolus can be made through a lumen of the guide catheter.

73. The system of claim 1, wherein the profile identifies a body lumen junction.

74. The system of claim 19, wherein the device is selected from the group consisting of a wire and a catheter.

75. The system of claim 19, wherein the device comprises a wire inserted through a guide catheter, where the infusion of a bolus can be made through a lumen of the guide catheter.

76. The system of claim 19 wherein the profile identifies a body lumen junction.

77. The method of claim 61, wherein the device is selected from the group consisting of a wire and a catheter.

78. The method of claim 61, wherein the profile identifies a body lumen junction.

79. The system of claim 8, wherein the device further comprises a distendable stent positioned around the balloon and a second pair of excitation electrodes and a second pair of detection electrodes positioned within an interior of the balloon.

80. The system of claim 19, wherein the conductance data is indicative of a change in voltage at the plurality of locations over the distance within the body lumen, wherein the change in voltage is proportional to a cross-sectional area of the body lumen.

81. The system of claim 37, wherein the conductance data is indicative of a change in voltage at the plurality of locations over the distance within the body lumen, wherein the change in voltage is proportional to a cross-sectional area of the body lumen.

* * * * *